(12) United States Patent
Jiang et al.

(10) Patent No.: US 6,596,497 B1
(45) Date of Patent: Jul. 22, 2003

(54) SCREENING OF ANTIVIRAL COMPOUNDS TARGETED TO THE HIV-1 GP41 CORE STRUCTURE

(75) Inventors: Shibo Jiang, Jackson Heights, NY (US); Asim K. Debnath, Fort Lee, NJ (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/525,874

(22) Filed: Mar. 14, 2000

Related U.S. Application Data

(60) Provisional application No. 60/124,907, filed on Mar. 17, 1999.

(51) Int. Cl.[7] .............................................. G01N 33/53
(52) U.S. Cl. ........................ 435/7.1; 424/160.1; 435/4; 435/5; 435/7.72; 435/7.92; 435/7.93; 435/7.94; 436/501; 530/388.1; 530/388.3; 530/389.1; 530/389.4
(58) Field of Search ........................... 424/133.1, 134.1, 424/160.1; 435/4, 5, 7.1, 7.5, 7.72, 7.92, 7.93, 7.94; 436/501; 530/388.1, 388.3, 389.1, 389.4

(56) References Cited

U.S. PATENT DOCUMENTS

| | | |
|---|---|---|
| 5,166,050 A | 11/1992 | Shriver et al. |
| 5,230,998 A | 7/1993 | Neurath et al. |
| 5,731,189 A | 3/1998 | Zolla-Pazner et al. |

(List continued on next page.)

FOREIGN PATENT DOCUMENTS

| | | |
|---|---|---|
| EP | 335 134 | 10/1989 |
| EP | 492 560 | 7/1992 |

OTHER PUBLICATIONS

Ryu et al. Development of an in vitro assay system for screening of gp41 inhibitory compounds. Molecules and Cells (1998) vol. 8, No. 6, pp. 717–723.*

Coligan et al. Induction of the immune system, In Current Protocols in Immunology, John Wiley and Sons, Inc. (1998).*

Shibo Jiang, Kang Lin and Min Lu, "A Conformation–Specific Monoclonal Antibody Reacting with Fusion–Active gp41 from the Human Immunodeficiency Virus Type 1 Envelope Glycoprotein", Journal of Virology, Dec. 1998, 10213–10217.

(List continued on next page.)

Primary Examiner—James Housel
Assistant Examiner—Ulrike Winkler
(74) Attorney, Agent, or Firm—Frishauf, Holtz, Goodman & Chick, P.C.

(57) ABSTRACT

A method for the screening of antiviral compounds targeted to the HIV gp41 core structure comprising capturing polyclonal antibodies from an animal other than a mouse directed against a trimer of a heterodimer containing an N-peptide and a C-peptide onto a solid-phase, mixing a compound to be tested with an N-peptide and then adding a C-peptide, adding the resultant mixture to the resultant polyclonal antibody coated solid-phase and then removing unbound peptides and unbound compound, adding a monoclonal antibody directed against the trimer of a heterodimer containing an N-peptide and a C-peptide and measuring the antibody binding of the monoclonal antibody. A method for inhibiting HIV-1 virus replication or infectivity in a patient by administering to the patient an antiviral compound targeted to the HIV-1 gp41 core structure selected from the group consisting of 7-[6-phenylamino-4[4-[(3,5-disulfo-8-hydroxynaphthyl)azo]-2-methoxy-5-methyl-phenylamino]-1,3,5-triazine-2-yl]-4-hydroxy-3-[(2-methoxy-5-sulfophenyl)azo]-2-naphthalene sulfonic acid and 5-[(4-chloro-6-phenylamino-1,3,5-triazine-2-yl)-amino]-4-hydroxy-3-[(4-methyl-5-sulfophenyl)azo]-2,7-naphthalene disulfonic acid.

4 Claims, 14 Drawing Sheets

U.S. PATENT DOCUMENTS

| | | | |
|---|---|---|---|
| 5,777,074 A | | 7/1998 | Cotropia |
| 5,798,206 A | | 8/1998 | Neurath et al. |
| 5,840,843 A | | 11/1998 | Jiang et al. |
| 6,150,088 A | * | 11/2000 | Chan et al. ............... 435/5 |
| 6,294,341 B1 | * | 9/2001 | Yu et al. ............... 435/7.1 |

OTHER PUBLICATIONS

Shibo Jiang and Asim K. Debnath, "A Salt Bridge Between an N–terminal Coiled Coil of gp41 and an Antiviral Agent Targeted to the gp41 Core Is Important for Anti–HIV–1 Activity", *Biochemical and Biophysical Research Communications*, 270, No. 1, p. 153–157 (2000).

Shibo Jiang and Asim K. Debnath, "Development of HIV Entry Inhibitors Targeted to the Coiled–Coil Regions of gp41", *Biochemical and Biophysical Research Communications*, 269, No. 3, p. 641–646 (2000).

Shibo Jiang, Lin Radigan and Li Zhang, "A Convenient Cell Fusion Assay for Rapid Screening for HIV Entry Inhibitors", *Progress in Biomedical Optics*, 1, No. 20, Jan. 26–27, 2000, p. 212–219.

Shibo Jiang, Kang Lin, Li Zhang, Asim K. Debnath, "A Screening Assay for Antiviral Compounds Targeted to the HIV–1 gp41 Core Structure Using a Conformation–Specific Monoclonal Antibody", *Journal of Virological Methods*, 80, p. 85–96 (1999).

Asim Kumar Debnath, Lin Radigan and Shibo Jiang, "Structure–Based Identification of Small Molecule Antiviral Compounds Targeted to the gp41 Core Structure of the Human Immunodeficiency Virus Type 1", *Journal of Medicinal Chemistry*, 42, No. 17, p. 3203–3209 (1999).

Hong Ji, Wei Shu, F. Temple Burling, Shibo Jiang and Min Lu, "Inhibition of Human Immunodeficiency Virus Type 1 Infectivity by the gp41 Core: Role of a Conserved Hydrophobic Cavity in Membrane Fusion", *Journal of Virology*, 73, No. 10, Oct. 1999, p. 8578–8586.

S. Jiang, N. Strick and A.R. Neurath, "Two Partially Overlapping Antiviral Peptides from the External Portion of HIV Type 1 Glycoprotein 41, Adjoining the Transmembrane Region, Affect the Glycoprotein 41 Fusion Domain", *Aids Research and Human Retroviruses*, 11, No. 2, 1995, p. 189–190.

Shibo Jiang and Kang Lin, "Effect of Amino Acid Replacements, Additions and Deletions of the Antiviral Activity on a Peptide Derived from the HIV–1 GP41 Sequence", *Peptide Research*, 8, No. 6, (1995), p. 345–348.

W. Weissenhorn, A. Dessen, S.C. Harrison, J.J. Skehel & D.C. Wiley, "Atomic Structure of the Ectodomain from HIV–1 gp41", *Nature*, 387, May 22, 1997, p. 426–430.

Jie Cao, Louise Bergeron, Eirik Helseth, Markus Thali, Heinrich Repke and Joseph Sodroski, "Effects of Amino Acid Changes in the Extracellular Domain of the Human Immunodeficiency Virus Type 1 gp41 Envelope Glycoprotein", *Journal of Virology*, 67, No. 5, May 1993, p. 2747–2755.

David C. Chan, Christine T. Chutkowski and Peter S. Kim, "Evidence That a Prominent Cavity in the Coiled Coil of HIV Type 1 gp41 is an Attractive Drug Target", *Proc. Natl. Acad. Sci. USA*, 95, pp. 15613–15617, Dec. 1998.

R.A. Furata, Carl T. Wild, Yongkai Weng and Carol D. Weiss, "Capture of an Early Fusion–Active Conformation of HIV–1 gp41", *Nature Structural Biology*, 5, No. 4, Apr. 1998, pp. 276–279.

Philip L. St. J. Jones, Thomas Korte and Robert Blumenthal, "Conformational Changes in Cell Surface HIV–1 Envelope Glycoproteins Are Triggered by Cooperation between Cell Surface CD4 and Co–receptors", *The Journal of Biological Chemistry*, 273, No. 1, Jan. 2, 1998, p. 404–409.

Andrew C. Good, Todd J.A. Ewing, Daniel A. Gschwend and Irwin D. Kuntz, "New Molecular Shape Descriptors: Application in Database Screening", *Journal of Computer–Aided Molecular Design*, 9, (1995) p. 1–12.

Debra M. Eckert, Vladimir N. Malashkevich, Lily H. Hong, Peter A. Carr and Peter S. Kim, "Inhibiting HIV–1 Entry: Discovery of D–Peptide Inhibitors that Target the gp41 Coiled–Coil Pocket", *Cell*, 99, Oct. 1, 1999, p. 103–115.

Shibo Jiang, Kang Lin, Nathan Strick and A. Robert Neurath, "Inhibition of HIV–1–Infection by a Fusion Domain Binding Peptide from the HIV–1 Envelope Glycoprotein GP41", *Biochemical and Biophysical Research Communications*, 195 No. 2, 1993, pp. 533–538.

Shibo Jiang, Kang Lin, Nathan Strick and A. Robert Neurath, "HIV–1 Inhibition by a Peptide", *Nature*, 365, Sept. 9, 1993, p. 113.

John B. Moore, Bradford A. Jameson, Robin A. Weiss and Quentin J. Sattentan, "The HIV–Cell Fusion Reaction" in *Viral Fusion Mechanisms*, Edited by Joe Bentz, CRC Press, Boca Raton, FL, 1993, pp. 233–289.

Yu Feng, Christopher C. Broder, Paul E. Kennedy and Edward A. Berger, "HIV–1 Entry Cofactor: Functional cDNA Cloning a Seven–Transmembrane, G Protein––Coupled Receptor", *Science*, 272 May 10, 1996, pp. 872–877.

William R. Gallaher, Judith M. Ball, Robert F. Garry, Mark C. Griffin and Ronald c. Montelaro, "A General Model for the Transmembrane Proteins of HIV and Other Retroviruses", *Aids Research and Human Retroviruses*, 5, No. 4, 1989, pp. 431–440.

Carl Wild, Terrence Oas, Charlene McDanal, Dani Bolognesi and Thomas Matthews, "A Synthetic Peptide Inhibitor of Human Immunodeficiency Virus Replication: Correlation Between Solution Structure and Viral Inhibition", *Proc. Natl. Acad. Sci. USA*, 89, pp. 10537–10541, Nov. 1992.

Carl T. Wild, Diane C. Shugars, Teresa K. Greenwell, Charlene B. McDanal and Thomas J. Matthews, "Peptides Corresponding to a Predictive α–Helical Domain of Human Immunodeficiency virus Type 1 GP41 are Potent Inhibitors of Virus Infection", *Proc. Natl. Acad. Sci. USA*, 91, Oct. 1994, pp. 9770–9774.

J. Michael Kilby, Sam Hopkins, Thomas M. Venetta, Betty DiMassimo, Gretchen A. Cloud, Jeanette Y. Lee, Leslie Alldredge, Eric Hunter Dani Bolognesi, Thomas Matthews, M. Ross Johnson, Martin A. Nowak, George M. Shaw and Michael S. Saag, "Potent Suppression of HIV–1 Replication in Humans by T–20, a Peptide Inhibitor of gp41–Mediated Virus Entry", *Nature Medicine*, 4, No. 11, Nov. 1998, pp. 1302–1307.

Min Lu, Stephen C. Blacklow and Peter S. Kim, "A Trimeric Structural Domain of the HIV–Transmembrane Glycoprotein", *Nature Structural Biology*, No. 12, Dec. 1995, pp. 1075–1082.

David C. Chan, Deborah Fass, James M. Berger and Peter S. Kim, "Core Structure of gp41 from the HIV Envelope Glycoprotein", *Cell*, 89, Apr. 18, 1997, pp. 263–273.

* cited by examiner

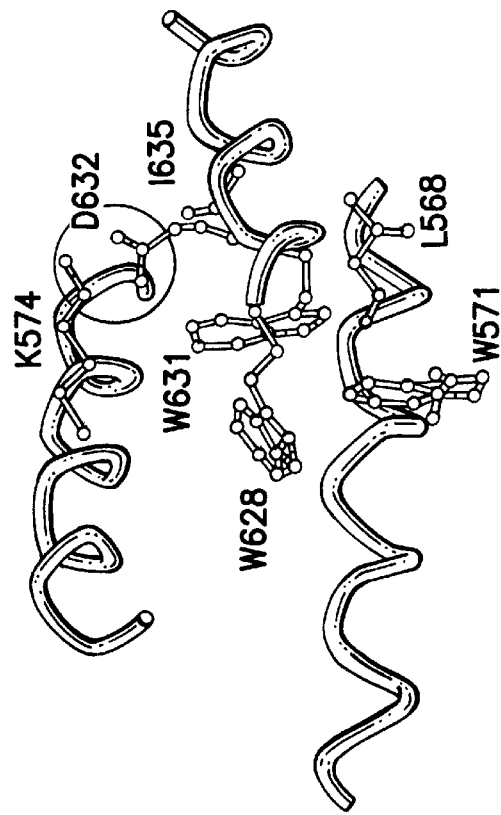
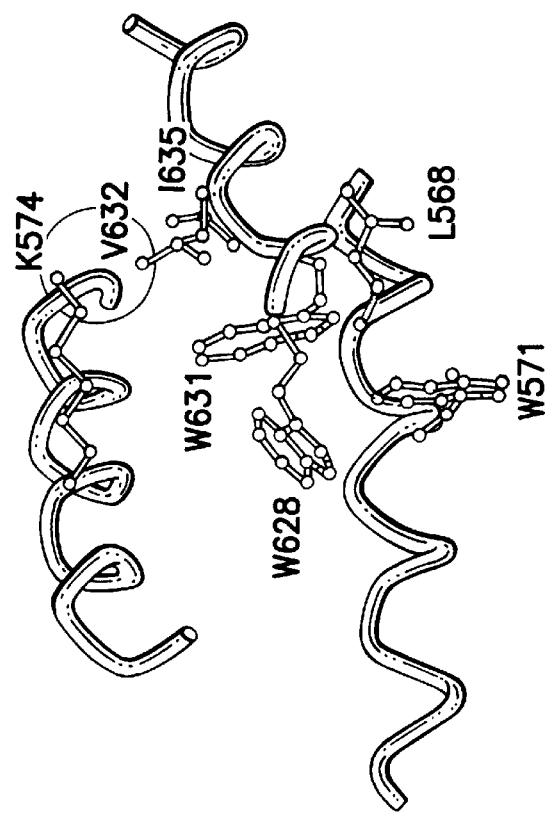
FIG. 14A
FIG. 14B

SEQUENCE LISTING

```
<160> NUMBER OF SEQ ID NOS: 3

<210> SEQ ID NO 1
<211> LENGTH: 6
<212> TYPE: PRT
<213> ORGANISM: Epitope recognized by human MAb 2F5
<220> FEATURE:
<222> LOCATION: 662..667

<400> SEQUENCE: 1

Glu Leu Asp Lys Trp Ala
1               5

<210> SEQ ID NO 2
<211> LENGTH: 50
<212> TYPE: PRT
<213> ORGANISM: NHR region of gp41
<220> FEATURE:
<222> LOCATION: 540..589

<400> SEQUENCE: 2

Gln Ala Arg Gln Leu Leu Ser Gly Ile Val
1               5                  10

Gln Gln Gln Asn Asn Leu Leu Arg Ala Ile
                15                  20

Glu Ala Gln Gln His Leu Leu Gln Leu Thr
                25                  30

Val Trp Gly Ile Lys Gln Leu Gln Ala Arg
                35                  40

Ile Leu Ala Val Glu Arg Tyr Leu Lys Asp
                45                  50

<210> SEQ ID NO 3
<211> LENGTH: 43
<212> TYPE: PRT
<213> ORGANISM: CHR region of gp41
<220> FEATURE:
<222> LOCATION: 624..666

<400> SEQUENCE: 3
```

-continued

```
Asn Asn Met Thr Trp Met Glu Trp Asp Arg
 1               5                    10

Glu Ile Asn Asn Tyr Thr Ser Leu Ile His
                 15                   20

Ser Leu Ile Glu Glu Ser Gln Asn Glu Gln
                 25                   30

Glu Lys Asn Glu Gln Glu Leu Leu Glu Leu
                 35                   40

Asp Lys Trp
```

SCREENING OF ANTIVIRAL COMPOUNDS TARGETED TO THE HIV-1 GP41 CORE STRUCTURE

CROSS-REFERENCE TO RELATED APPLICATION

The present application claims the benefit of Provisional Application Ser. No. 60/124,907, filed Mar. 17, 1999, wherein priority under 35 USC 119(e) is claimed.

GOVERNMENT RIGHTS

This invention was made with United States government support under Grant AI42693 from the National Institute of Health. The United States government has certain rights in this invention.

BACKGROUND OF THE INVENTION

1. Field of the Invention

The present invention is directed to a screening assay for antiviral compounds targeted to the HIV-1 gp41 core structure utilizing a conformation-specific monoclonal antibody, which is reactive with fusion active gp41 from human immunodeficiency virus type 1 ("HIV-1") envelope glycoprotein. The present invention further relates to antiviral compounds targeted to the gp41 core structure of HIV-1.

2. Background Information

The infection of human immunodeficiency virus type I (HIV-1) is initiated by binding of the envelope glycoprotein (Env) surface subunit gp120 to both CD4 and particular chemokine receptors (i.e., CXCR4 and CCR5, etc.) on target cells. The Env transmembrane subunit gp41 concurrently dissociates from gp120 and then mediates the fusion of the viral and cellular membranes (Moore, J. P., B. A. Jameson, R. A. Weiss, and Q. J. Sattentau. 1993, "The HIV-cell fusion reaction", In *Viral Fusion Mechanisms*, J. Bentz, editors. CRC Press, Boca Raton. pp. 233–289; Berger, E. A. 1997, "HIV-1 entry and tropism: the chemokine receptor connection", *AIDS*, 11 (Supp. A): S3-16; Hunter, E., 1997, "gp41, a multifunctional protein involved in HIV entry and pathogenesis", In *Human Retroviruses and AIDS*, 1997; Korber, B., Hahn, B., Foley, B., Mellors, J. W., Leitner, T., Myers, G., McCutchan, F., Kuiken, C. editors, Los Alamos National Laboratory, Los Alamos, N.M. p. 111-55–111-73; and Chan, D. C. and P. S. Kim, 1998, "HIV entry and its inhibition", *Cell*, 93, 681–684).

HIV-1 gp41 is composed of three domains, an extracellular domain (ectodomain), a transmembrane domain and an intracellular domain (endodomain). The gp41 ectodomain contains three major functional regions, i.e., the fusion peptide located at the N-terminus of gp41, followed by two 4-3 heptad repeats adjacent to the N- and C-terminal portions of the gp41 ectodomain, designated NHR (N-terminal heptad repeat) and CHR (C-terminal heptad repeat), respectively. The N- and C-terminal repeats were also named as "HR1" and "HR2", respectively, by Rimsky, L. T., D. C. Shugars and T. J. Matthews, *J. Virol.*, 72, 986–993.

Both NHR and CHR regions consist of hydrophobic amino acid sequences predicted to form α-helices, denoted N and C helix (Caffrey, M., M. Cal, J. Kaufman, S. J. Stahl, P. T. Wingfield, D. G. Covell, A. M. Gronenborn, and G. M. Clore, 1998, "Three-dimensional solution structure of the 44 kDa ectodomain of SIV gp41", *EMBO J*, 17, 4572–4584), which may function as essential structures required for oligomerization of gp41 and for conformational changes during the process of membrane fusion between HIV-1 and target cells (Gallaher, W. R., J. M. Ball, R. F. Garry, M. C. Griffin, and R. C. Montelaro, 1989, "A general model for the transmembrane proteins of HIV and other retroviruses", *AIDS Res. Hum. Retroviruses*, 5, 431–440; Delwart, E. L., G. Mosialos, and T. Gilmore, 1990, "Retroviral envelope glycoprotein contain a leucine zipper-like repeat", *AIDS Res. Hum. Retroviruses*, 6, 703–706; Wild, C., T. Oas, C. McDanal, D. Bolognesi, and Matthews, T., 1992, "A synthetic peptide inhibitor of human immunodeficiency virus replication: correlation between solution structure and viral inhibition", *Proc. Natl. Acad. Sci. USA*, 89, 10537–10541; Bernstein, H. B., S. P. Tucker, S. R. Kar, S. A. McPherson, D. T. McPherson, J. W. Dubay, J. Lebowitz, R. W. Compans, and E. Hunter, 1995, "Oligomerization of the hydrophobic heptad repeat of gp41", *J. Virol.*, 69, 2745–2750).

Peptides derived from the NHR and CHR regions of gp41, designated N- and C-peptides (Chan, D. C, and P. S. Kim, 1998, "HIV entry and its inhibition", *Cell*, 93, 681–684), have potent antiviral activity against HIV-1 infection (Jiang, S., K. Lin, N. Strick, and A. R. Neurath, 1993, "HIV-1 inhibition by a peptide", *Nature*, 365, 113; Wild, C. T., D. C. Shugars, T. K. Greenwell, C. B. McDanal, and T. J. Matthews, 1994, "Peptides corresponding to a predictive alpha-helical domain of human immunodeficiency virus type I gp41 are potent inhibitors of virus infection", *Proc. Natl. Acad. Sci. USA*, 91, 9770–9774; and Lu, M., S. C. Blacklow, and P. S. Kim, 1995, "A trimeric structural domain of the HIV-1 transmembrane glycoprotein", *Nat. Struct. Biol.*, 2, 1075–1082). Previous studies suggest that these peptides inhibit the membrane fusion step of HIV-1 infection, in a dominant-negative manner, by binding to viral gp41 (Chen, C. R, T. J. Matthews, C. B. McDanal, D. P. Bolognesi, and M. L. Greenberg, 1995, "A molecular clasp in the human immunodeficiency virus (HIV) type 1 TM protein determines the anti-HIV activity of gp41 derivatives: implication for viral fusion", *J. Virol.*, 69, 3771–3777; and Furuta, R., C. T. Wild, Y. Weng, and C. D. Weiss, 1998, "Capture of an early fusion-active conformation of HIV-1 gp41", *Nat. Struct. Biol.*, 5:276–279).

Limited proteolysis of a recombinant fragment of the gp41 ectodomain generated an N-peptide and a C-peptide, designated N-51 (spanning residues 540–590) and C-43 (residues 624–666). These two peptides overlap mostly the NHR and CHR regions. Several other N- and C-peptides (i.e., N-36, N-34, C-34 and C-28) were also produced (Lu, M. and P. S. Kim, 1997, "A trimeric structural subdomain of the HIV-1 transmembrane glycoprotein", *J. Biochem. Struct. Dynamic*, 15:465–471). N- and C-peptides mixed at equimolar concentrations form stable α-helical trimers of antiparallel heterodimers, representing the fusion-active (fusogenic) core domain of gp41. Crystallographic studies showed that this core domain is a six-stranded helical bundle. Three N helices associate to form the internal coiled-coil trimer via interaction of the residues at "a" positions in the wheel of one N helix with those at "d" positions (see FIGS. 2 and 3) in that of another N helix. Three C helices pack obliquely against the outside grooves of the N helix trimer by the interaction of residues at "a" and "d" positions in C helices with those at "e" and "g" positions (see FIGS. 2 and 3) in N helices, respectively (Chan, D. C., D. Fass, J. M. Berger, and P. S. Kim, 1997, "Core structure of gp41 from the HIV envelope glycoprotein", *Cell*, 89, 263–273; Weissenhorn, W., A. Dessen, S. C, Harrison, I. I. Skehel, and D. C. Wiley, 1997, "Atomic Structure of the Ectodomain from HIV-1 gp41", *Nature*, 387, 426–428; and Tan, K., I. Liu, I. Wang, S. Shen, and M. Liu, 1997, "Atomic structure of a thermostable subdomain of HIV-1 gp41", *Proc. Natl. Acad. Sci. USA*, 94, 12303–12308).

The residues at these interaction sites are highly conserved and mutations of these residues may disrupt the six-stranded core structure and abolish HIV-1 infectivity (Cao, J., L. Bergeron, E. Helseth, M. Thali, H. Repke, and I. Sodroski, 1993, "Effects of amino acid changes in the extracellular domain of the human immunodeficiency virus type 1 gp41 envelope glycoprotein", *J. Virol.*, 67, 2747–2755; Chen, S. S., C. N. Lee, W. R. Lee, K. Mcintosh, and T. H. Lee, 1993, "Mutational analysis of the leucine zipper-like motif of the human immunodeficiency virus type 1 envelope transmembrane glycoprotein", *J. Virol.*, 67, 3615–3619; Wild, C., I. W. Dubay, T. Greenwell, T. Baird, Jr., I. G. Oas, C. McDanal, F. Hunter, and T. Matthews, 1994, "Propensity for a leucine zipper-like domain of human immunodeficiency virus type 1 gp41 to form oligomers correlates with a role in virus-induced fusion rather than assembly of the glycoprotein complex", *Proc. Natl. Acad. Sci. USA*, 91, 12676–12680; Poumbourios, P., K. A. Wilson, R. I. Center, R. El Ahmar, and B. E. Kemp, 1997, "Human immunodeficiency virus type 1 envelope glycoprotein oligomerization requires the gp41 amphipathic alpha-helical/leucine zipper-like sequence", *J. Virol.*, 71, 2041–2049).

Each of the grooves on the surface of the N helices has a deep cavity that accommodates three conserved hydrophobic residues (W628, W631 and I635) in C helices. These highly conserved deep hydrophobic cavities have been suggested as attractive targets for development of antiviral lead compounds that block HIV-1-mediated membrane fusion and HIV-1 infection.

Several antiviral drugs targeted to HIV-1 reverse transcriptase (RT) and protease have been approved by the US Food and Drug Administration (FDA) in recent years for the treatment of HIV-1 infection and AIDS (Carpenter, C. C., M. A. Fischl, S. M. Hammer, M. S. Hirsch, D. M. Jacobsen, D. A., Katzenstein, J. S. Montaner, D. D. S., M. S. Richman, R. T. Schooley, M. A. Thompson, S. Vella, P. G. Yeni, and P. A. Volberding, 1998, "Antiretroviral therapy for HIV infection in 1998: updated recommendations of the International AIDS Society USA Panel", *JAMA*, 280, 78–86). Combination therapy using these two types of inhibitors has been remarkably successful in reducing viral load and has lead to a decline in morbidity and mortality (Markowitz, M., M. Saag, W. G. Powderly, A. M. Hurley, A. Hsu, J. M. Valdes, D., Henry, F. Sattler, A. La Marca, Leonard J. M., and D. D. Ho, 1995, "A preliminary study of ritonavir, an inhibitor of HIV-1 protease, to treat HIV-1 infection", *N. Engl. J. Med.*, 333, 1534–1539; Detels, R., A. Munoz, G. McFarlane, L. A. Kingsley, J. B. Margolick, J. Giorgi, L. X. Schrager, J. Phair, and for the Multicenter AIDS Cohort Study investigators, 1998," "Effectiveness of potent antiretroviral therapy on time to AIDS and death in men with known HIV infection duration", *JAMA*, 280, 1497–1503; Hogg, R. S., S. A. Rhone, B. Yip, C. Sherlock, B. Conway, M. T. Schechter, M. V. O'Shaughnessy, and J. S. Montaner, 1998, "Antiviral effect of double and triple drug combinations amongst HIV-infected adults: lessons from the implementation of viral load-driven antiretroviral therapy", *AIDS*, 12, 279–284; Hogg, R. S., K. V. Heath, B. Yip, K. J. Craib, M. V. O'Shaughnessy, M. T. Schechter, and I. S. Montaner, 1998, "Improved survival among HIV-infected individuals following initiation of antiretroviral therapy", *JAMA*, 279, 450–454; Palella, F. J.Jr., K. M. Delaney, A. C. Moorman, M. O. Loveless, J. Fuhrer, G. A. Satten, D. J. Aschman, and S. D. Holmberg, 1998, "Declining morbidity and mortality among patients with advanced human immunodeficiency virus infection, HIV Outpatient Study Investigators", *N. Eng. J. Med.*, 338, 853–860). However, these drugs have a number of shortcomings, namely, (1) the emergence of HIV-1 mutant strains having single or multiple resistance to the drugs used (Gunthard, H. F., J. K. Wong, C. C. Ignacio, J. C. Guatelli, N. L. Riggs, D. V. Havlir, and D. D. Richman, 1998, "Human immunodeficiency virus replication and genotypic resistance in blood and lymph nodes after a year of potent antiretroviral therapy", *J. Virol.*, 72, 2422–2428; Richman, D. D., 1996, "Antiretroviral drug resistance: mechanisms, pathogenesis, clinical significance", *Adv. Exp. Med. Biol.*, 394, 383–395; Wong, J. K., H. F. Gunthard, D. V. Havlir, Z. Q. Zhang, A. T. Haase, C. C. Ignacio, S. Kwok, E. Emini, and D. D. Richman, 1997, "Reduction of HIV-1 in blood and lymph nodes following potent antiretroviral therapy and the virologic correlates of treatment failure", *Proc. Natl. Acad. Sci. USA*, 94, 12574–12579); (2) Adverse side effects; and (3) high cost (Montaner, J. S., R. S. Hogg, A. E. Weber, A. H. Anis, M-V. O'Shaughnessy, and M. T. Schechter, 1998, "The costs of triple-drug anti-HIV therapy for adults in the Americas", *JAMA*, 279, 1263–1264). In addition, these drugs are targeted to later stages of infection. Therefore, it is essential to develop compounds with higher effectiveness and lower side effects which can prevent early steps of HIV-1 infection.

The C-peptides block in vitro HIV-1 infection and cell fusion at nM concentrations. In a recent phase I/II clinical trial in humans, T-20, one of the C-peptides showed potent in vivo inhibition of HIV-1 replication, resulting in viral load reduction comparable to that obtained by the 3-4 combination therapies with RT and protease inhibitors (Kilby, J. M., S. Hopkins, T. M. Venetta, B. DiMassimo, G. A. Cloud, J. Y. Lee, L. Alldredge, E. Hunter, I. D. Lambert, D. Bolognesi, T. Matthews, M. R. Johnson, M. A. Nowak, G. M. Shaw, and M. S. Saag, 1998, "Potent suppression of HIV-1 replication in humans by T-20, a peptide inhibitor of gp41-mediated virus entry", *Nature Med.,* 4, 1302–1367). Despite this early success, the application of this peptide therapy may be limited due to the high production cost of the peptide and lack of its oral availability. Thus, identification of small molecule inhibitors reacting with the same or overlapping target sites on gp41 recognizing the antiviral peptides needed.

U.S. Pat. No. 5,840,843 describes a synthetic HIV-1 polypeptide which comprises an amino acid sequence corresponding to the amino acid sequence of the envelope glycoprotein of HIV-$1_{IIIB}$ virus from the amino acid residue 600 to the amino acid residue 862. U.S. Pat. No. 5,840,843 refers to "peptide (637–666)", based on its sequence in gp41 (amino acid residues 637–666). The sequence was numbered according to Ratner's publication (*Nature,* 313, 227–284, 1985). However, most AIDS researchers later numbered the gp41 sequence according to a book entitled "Human Retrovirus and AIDS". According to this book, the sequence of "peptide (637–666)" was renumbered as "630–659" and the peptide was renamed as "SJ-2176". This peptide has 30 residues overlapping the peptide "C34" (628–661).

EP 335,134 describes a mouse monoclonal antibody to human immunodeficiency virus gp41 protein.

U.S. Pat. No. 5,777,074 and EP 492,560 describe a method for neutralizing HIV-1 utilizing a human monoclonal antibody directed against the transmembrane glycoprotein (gp41) of HIV-1 (also see U.S. Pat. No. 5,459,060).

U.S. Pat. No. 5,166,050 describes monoclonal antibodies and peptides useful in treating and diagnosing HIV infections.

SUMMARY OF THE INVENTION

It is an object of the present invention to provide methods for the screening of antiviral compounds targeted to the HIV-1 gp41 core structure.

It is also an object of the present invention to provide a conformation-specific monoclonal antibody which reacts with fusion-active gp41 from the HIV-1 envelope glycoprotein.

It is a further object of the present invention to provide a screening assay for antiviral compounds targeted to the HIV-1 gp41 core structure using the conformation-specific monoclonal antibody which reacts with fusion-active gp41 from the HIV-1 envelope glycoprotein.

It is a still further object of the present invention to provide compounds which are effective against HIV-1 infection.

It is another object of the present invention to provide methods for inhibiting HIV-1 virus replication or infectivity or treating HIV-1 infection in a subject without inducing undesirable immunosuppressive effects.

The above objects, as well as other objects, aims and advantages, are satisfied by the present invention.

The present invention concerns methods for the screening of antiviral compounds targeted to the HIV-1 gp41 core structure using (i) polyclonal and monoclonal antibodies, and only (ii) monoclonal antibodies.

A first method for the screening of antiviral compounds targeted to the HIV-1 gp41 core structure, which involves the use of polyclonal and monoclonal antibodies, comprises:

(a) capturing polyclonal antibodies from an animal other than a mouse, directed against a trimer of a heterodimer containing an N-peptide and a C-peptide, onto a solid-phase to form a polyclonal antibody coated solid-phase;

(b) mixing a compound to be tested with an N-peptide, and then adding a C-peptide thereto;

(c) adding the mixture from step (b) to the polyclonal antibody coated solid-phase form step (a), and then removing unbound peptides and unbound compound;

(d) adding a monoclonal antibody directed against the trimer of a heterodimer containing an N-peptide and a C-peptide, and (e) measuring the binding of the monoclonal antibody (for example, by sequentially adding biotin labeled anti-mouse IgG, streptavidin or avidin labeledenzyme, and a substrate for generating detectable color).

A second method for the screening of antiviral compounds targeted to the HIV-1 gp41 core structure, which involves the use of monoclonal antibodies, comprises:

(a) capturing a C-peptide onto a solid-phase to form a C-peptide coated solid-phase;

(b) mixing a compound to be tested with an N-peptide;

(c) adding the mixture from step (b) to the C-peptide coated solid-phase from step (a), and then removing unbound peptide and unbound compound;

(d) adding a monoclonal antibody directed against a trimer of a heterodimer containing an N-peptide and a C-peptide, and (e) measuring the binding of the monoclonal antibody (for example, by sequentially adding biotin labeled anti-mouse IgG, streptavidin or avidin labeled enzyme, and a substrate for generating detectable color).

A third-method for the screening of antiviral compounds targeted to the HIV-1 gp41 core structure, which involves the use of monoclonal antibodies, comprises:

(a) capturing an N-peptide onto a solid-phase to form an N-peptide coated solid-phase;

(b) mixing a compound to be tested with a C-peptide;

(c) adding the mixture from step (b) to the N-peptide coated solid-phase from step (a), and then removing unbound peptide and unbound compound;

(d) adding a monoclonal antibody directed against a trimer of heterodimer containing an N-peptide and a C-peptide, and (e) measuring the binding of the monoclonal antibody (for example, by sequentially adding biotin labeled anti-mouse IgG, streptavidin or avidin labeled enzyme, and a substrate for generating detectable color).

The present invention also concerns a monoclonal antibody which reacts with the fusion-active gp41 core structure and which binds specifically to a trimer of a heterodimer formed by an N-peptide and a C-peptide, but not to the individual N-peptide and C-peptide. The present invention is further directed to a conformation-specific monoclonal antibody which binds specifically to the oligomeric forms of gp41 and to the surfaces of HIV-1 infected cells only in the presence of soluble CD4.

The present invention also relates to a method for the screening of antiviral compounds targeted to the HIV-1 gp41 core structure by utilizing the conformation-specific monoclonal antibody described herein in an assay, such as an enzyme-linked immunosorbent assay (ELISA).

The present invention is further directed to a method of inhibiting HIV-1 virus replication or infectivity in cells comprising contacting the cells with a compound selected from the group consisting of 7-[6-phenylamino-4-[4-[(3,5-disulfo-8-hydroxynaphthyl)azo]-2-methoxy-5-methylphenylamino]-1,3,5,triazine-2-yl]-4-hydroxy-3-[(2-methoxy-5-sulfophenyl)azo]-2-naphthalene sulfonic acid and 5-[(4-chloro-6-phenylamino-1,3,5-triazine-2-yl)-amino]-4-hydroxy-3-[(4-methyl-6-sulfophenyl)azo]-2,7-naphthalene disulfonic acid.

The present invention also concerns a method of inhibiting HIV-1 virus replication or infectivity in a patient or for treating a patient infected with HIV-1 comprising administering to the patient an effective anti-HIV-1 amount of at least one pharmaceutically active compound selected from the group consisting of 7-[6-phenylamino-4-[4-[(3,5-disulfo-8-hydroxynaphthyl)azo]-2-methoxy-5-methylphenylamino]-1,3,5,triazine-2-yl]-4-hydroxy-3-[(2-methoxy-5-sulfophenyl)azo]-2-naphthalene sulfonic acid and 5-[(4-chloro-6-phenylamino-1,3,5-triazine-2-yl)-amino]-4-hydroxy-3-[(4-methyl-6-sulfophenyl)azo]-2,7-naphthalene disulfonic acid, alone, or in combination with a pharmaceutically acceptable carrier.

BRIEF DESCRIPTION OF THE DRAWINGS

For the purposes of illustrating the invention, there is shown in the drawings forms which are presently preferred. It is to be understood, however, that the present invention is not limited to the precise arrangements and instrumentalities depicted in the drawings.

FIG. 5A shows the binding of NC-1 to complexes formed by N- and C-peptides. FIG. 5B shows that NC-1 reactivity is abolished by point mutations that disrupt the six-helix core formations. FIG. 5C shows the reactivity of NC-1 to the core domains formed by N-36 and C-peptides derived from the transmembrane glycoprotein sequences of different HIV strains.

FIGS. 7A and 7B show the results for HIV-1$_{IIIB}$-infected cells which were reacted with the monoclonal antibodies NC-1 (according to the present invention) and 2F5, respectively, in the presence or absence of sCD4 (10 μg/ml). FIG. 7C shows the binding of NC-1 to HIV-2$_{ROD}$-infected cells.

FIGS. 14A to 14D are schematic representations of the hydrophobic and ionic interactions of N-peptides with C-peptides and two small compounds, namely ADS-J1 (see TABLE 1 hereinafter) and ADS-J13 (see TABLE 1 hereinafter). FIG. 14A shows the interaction between C34 and N36 (only the pocket region is shown for clarity). Hydrophobic interaction between residues Trp 628, Trp 631 and Ile 635 in C34 and residues Leu 568, and Trp 571 in N36 and the ionic interaction between Asp 632 in C34 and Lys 574 in N36 form a salt bridge (circled). FIG. 14B shows the interaction between N36 and an analog of C34 with a non-conserved mutation (D632V). Although D632V has hydrophobic residues to interact with the hydrophobic residues in N36, it does not have a negatively charged residue at position 632 to form a salt bridge with Lys 574 in N36 (circled). FIG. 14C shows the interaction between N36 and ADS-J1. The hydrophobic groups (phenyl and naphthalene) in ADS-J1 interact with the hydrophobic residues in N36. ADS-J1 also has a negatively charged group (sulfonic acid) which is in close proximity to Lys 574 in N36. A salt bridge may be formed through this ionic interaction (circled). FIG. 14D shows the interaction between N36 and ADS-J13. The inactive compound ADS-J13 has hydrophobic groups to interact with the hydrophobic residues in N-peptides, but lacks the important ionic interaction site to form a salt bridge with Lys 574 (circled).

DETAILED DESCRIPTION OF THE INVENTION

The gp41 of HIV-1 consists of an ectodomain, a transmembrane domain (TM) and a cytoplasmic domain (CP). The ectodomain contains three major functional regions, i.e., a fusion peptide (FP) and two heptad repeat regions adjacent to the N- and C-terminii, namely, the N-terminal heptad repeat (NHR), and the C-terminal heptad repeat (CHR). The residue numbers of each region correspond to their positions in gp160.

The peptides derived from gp41 NHR and CHR regions are designated "N-peptide" and "C-peptide", respectively. As used herein, a "C-peptide" is a peptide having at least five continuous amino acids in the CHR of HIV-1 gp41; and an "N-peptide" is a peptide having at least five continuous amino acids in the NHR of HIV-1 gp41. N- and C-peptides are potent inhibitors of HIV-1 infection and can interact with each other to form the six-stranded coiled-coil representing the fusogenic core structure of gp41.

Figure 1:
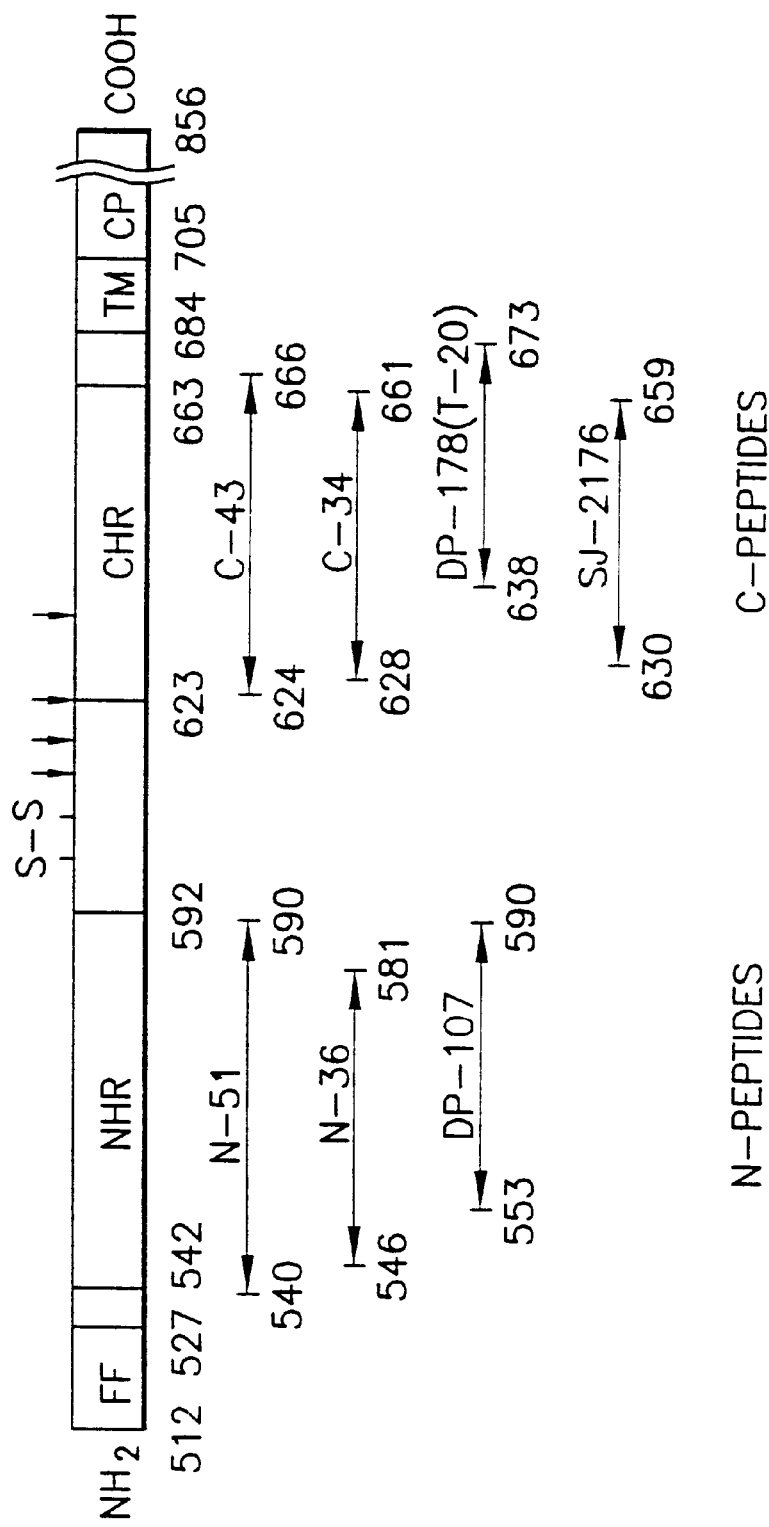
FIG. 1 is a schematic representation of gp41, including N- and C-peptides, the disulfide bond, and for potential N glycosylation sites.

FIG. 1 shows a schematic representation of HIV-1$_{HXB2}$ gp41.

Figure 2:
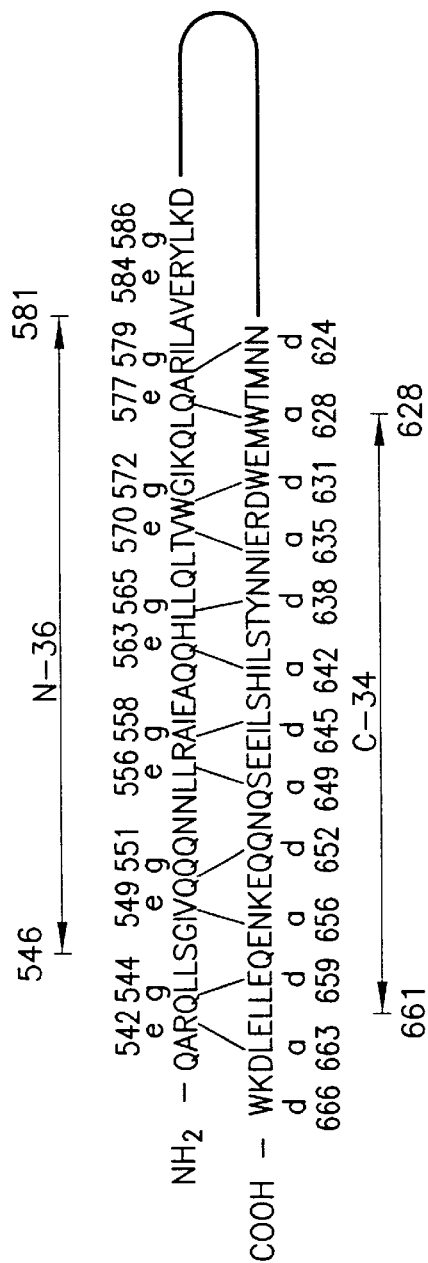
FIG. 2 is a schematic diagram showing the interaction between the NHR and CHR regions of gp41.

FIG. 2 shows the interaction between the NHR and CHR regions of gp41. The residues located at the interaction sites are labeled with letters indicating their positions in the α-helical wheel. For simplification, only one gp41 molecule is shown in FIG. 2.

Figure 3:
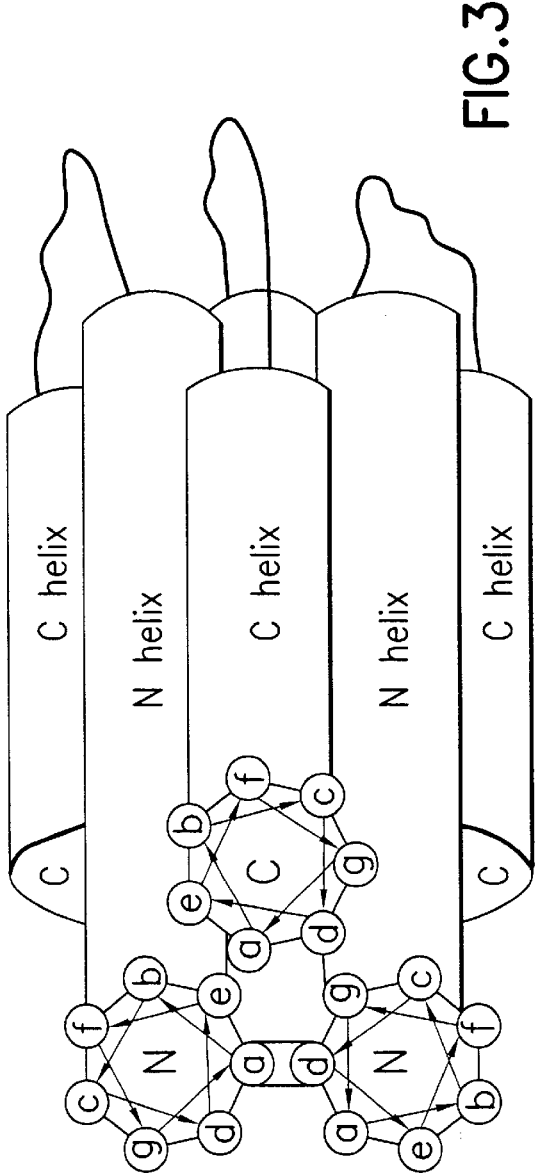
FIG. 3 is a schematic diagram showing the six-stranded coiled-coil domain of fusion-active gp41.

FIG. 3 is an illustration of the six-stranded coiled-coil domain of gp41. Three parallel N helices associate to form the internal α-helical trimer via the interactions between the residues at the "a" and "d" positions. Three C helices pack in the grooves on the surface of N helical trimer in the antiparallel fusion. The helical wheel representation of two N helices and one C helix is shown to indicate the interaction sites in the N and C helices, i.e., the residues at "a" positions in one C helix interact with those at "e" positions in one N helix and the residues at "d" positions in the same C helix associate with those at "g" positions in another N helix.

The monoclonal antibodies of the present invention (a specific one of which is designated as "NC-1" or "MAb NC-1") are produced by immunization of a mouse with a subdomain of the gp41 core, consisting of peptides N-36 and C-34 connected by a six-residue hydrophilic linker ("L6"), designated N36(L6)C34. This monoclonal antibody specifically recognizes discontinuous epitopes presented on the six-helix subdomain formed by the association of the N- and C-peptides and binds to oligomeric forms of gp41 expressed on the HIV-1 infected cells in the presence of soluble CD4.

The monoclonal antibody of the present invention specifically binds to the complex formed by the N- and C-peptides, but not to the individual peptides. Enzyme-linked immunosorbent assays were developed by the present inventors using such monoclonal antibody for detecting the complex formed by the N- and C-peptides and for the screening of organic compounds for antiviral agents that may interfere with complex formation and inhibit HIV-1 infection.

Without wishing to be bound by any particular theory of operability, the principle of the screening method of the present invention is based on the fact that the interaction between N- and C-peptides leads to formation of a six-stranded fusion-active core domain which can be specifically recognized by the monoclonal antibody defined herein, such as MAb NC-1. Therefore, any compounds that interact with the N or C-peptides and interfere with the formation of the six-helix complex may inhibit the HIV-1-mediated membrane fusion.

Figure 5A:
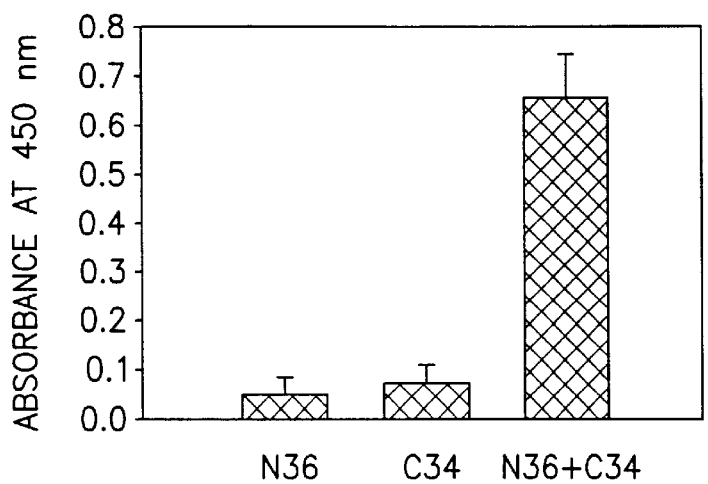
FIGS. 5A to 5C are graphs showing the reactivity of NC-1 with gp41 core domains.
Figure 8:
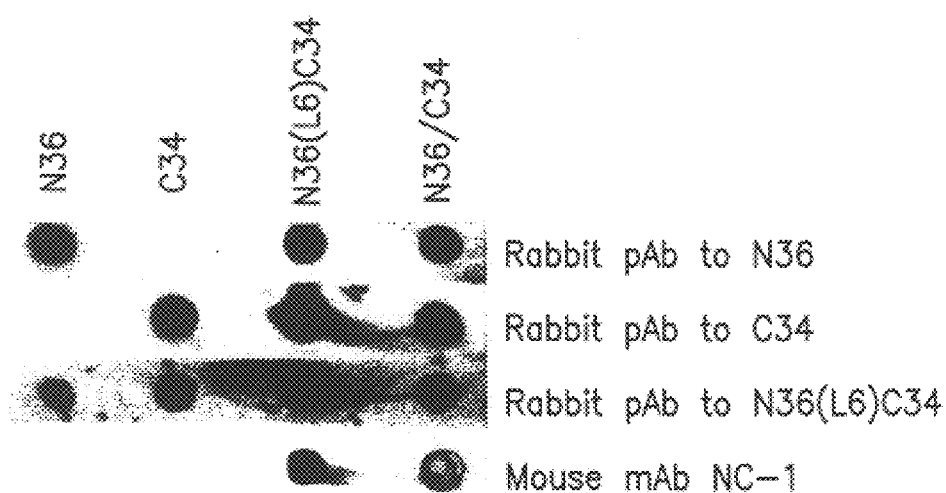
FIG. 8 shows the results of a dot blot assay concerning the binding to peptide and peptide complexes by MAb NC-1 and polyclonal antibodies (PAbs) directed against N- and C-peptides and an N-peptide/C-peptide complex.
Figure 10:
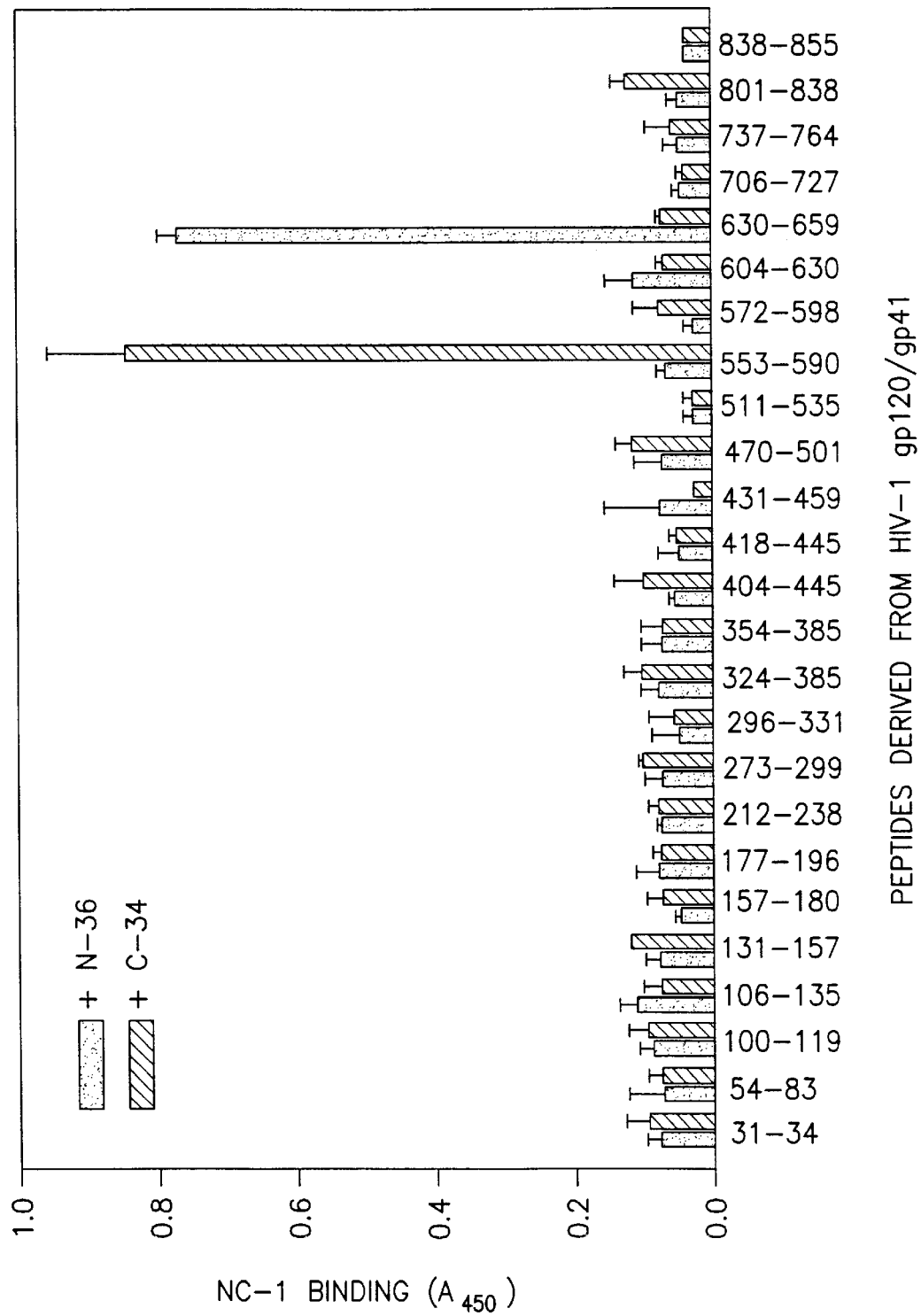
FIG. 10 is a graph showing the detection by MAb NC-1 of complexes formed by N-36 or C-34 with other synthetic peptides derived from HIV-1 gp120/gp41.

To validate the screening method of the present invention, it is necessary to determine whether: (1) the C-peptides specifically interact with N-peptides to form the six-stranded complexes; (2) the monoclonal antibody of the present invention and particularly monoclonal antibody NC-1 specifically binds to these complexes; and (3) the ability of the C-peptides to form the α-helical complexes with the N-peptides is related to their anti-HIV-1 activity. The results generated by the present inventors showed that the C-peptide (C-34) formed a NC-1 detectable complex with only a peptide (DP-107) derived from the gp41 NHR region (see FIG. 1A), but not with peptides from other regions of gp120/gp41. Similarly, the N-peptide (N-36) formed a complex with only a peptide (SJ-2176) overlapping the sequence within the CHR region of gp41 (FIG. 10). These results confirm that C-peptides or the CHR region interact with the N-peptides or the NHR region of gp41 to form the unique trimeric, α-helical coiled-coil structures (Wild, C., T. Greenwell, D. Shugars, L. Rimsky-Clarke, and T. Matthews, 1995, "The inhibitory activity of an HIV type 1 peptide correlates with its ability to interact with a leucine zipper structure", *AIDS Res. Hum. Retroviruses*, 11:323–325). The monoclonal antibody of the present invention, particularly MAb NC-1, binds only to the complexes formed by the N- and C-peptides, not to the individual peptides (FIGS. 5A and 8). Comparison of the wild-type and mutant C-peptides showed that the ability of these C-peptides to associate with the N-peptides is strongly correlated with their inhibitory activity against HIV-1-mediated membrane fusion. These results indicate that the ELISA methods described herein using the monoclonal antibody of the present invention, particularly monoclonal antibody NC-1, are applicable to screening of compounds for inhibitors of the interaction between N- and C-peptides.

The monoclonal antibodies of the present invention are produced by immunization of a mouse with a subdomain of the gp41 core, consisting of peptides N-36 and C-34 connected by a six-residue hydrophilic linker ("L6"), designated N36(L6)C34, which is a specific monoclonal antibody, designated as "NC-1" or "MAb NC-1". This monoclonal antibody specifically recognizes discontinuous epitopes presented on the six-helix subdomain formed by the association of the N- and C-peptides and binds to oligomeric forms of gp41 expressed on the HIV-1 infected cells in the presence of soluble CD4.

Murine hybridoma NC-1 (anti HIV-1 gp41 core) was deposited with the American Type Culture Collection ("ATCC") of Manassas, Va. 20110-2209 USA. The deposit was received on Mar. 3, 2000 and the culture was found to be viable on Mar. 17, 2000. The deposit was made pursuant to the Budapest Treaty. The deposit was given the accession number of PTA-1448.

An ELISA method according to the present invention, namely a sandwich ELISA method, comprises:

(1) coat plate with antibodies (IgG) from an animal (for example, a rabbit), other than mouse, immunized with a complex containing N- and C-peptides [N36(L6) C34];

(2) remove unbound antibodies (i.e, by washing);

(3) mix compounds to be tested at graded concentrations with N-peptide (N36)(2 μM) and incubated at desirable conditions, such as 37° C., 30 minutes;

(4) add C-peptide (C34)(2 μM) and incubated at desirable conditions such as 37° C., 30 minutes;

(5) add the mixture to the antibody-coated wells and incubate at desirable conditions such as 37° C. for 1 hour;

(6) remove unbound compounds and peptides (i.e., by washing);

(7) add the (mouse) monoclonal antibody of the present invention, particularly NC-1, and incubate at desirable conditions such as 37° C. for 1 hour;

(8) remove unbound antibody (i.e., washing);

(9) add biotin-labelled (e.g., goat) anti-mouse IgG and incubate at desirable conditions such as 37° C. for 1 hour;

(10) remove unbound antibody (i.e. by washing);

(11) add streptavidin (or avidin)-labelled enzyme (horseradish peroxidase) and incubate at desirable conditions such as 37° C. for 1 hour;

(12) remove unbound enzyme (i.e., by washing);

(13) add a substrate to generate detectable color (such as TMB: 3,3',5,5'-tetramethylbenzidine) and incubate at desirable conditions such as 37° C. for 15 minutes;

(14) add an acid such as $H_2SO_4$ to stop the reaction; and

(15) read the optical density (OD) at 450 nm (reference at 570) by an ELISA reader.

In the screening methods described hereinabove, enzyme systems can be conjugated with anti-mouse IgG or monoclonal antibody NC-1 directly, other than using the biotin-avidin system. Also, instead of an ELISA, an immunofluorescent assay ("IFA") using a dye (such as fluorescein isothiocyanate or rhodamine) or a radioimmunoassay (RIA) can be utilized.

Accordingly, the label for use in the screening methods according to the present invention can be any chemical group or residue having a detectable physical or chemical property. Such labels have been well developed in the field of immunoassays and in general any label useful in such methods can be applied to the present invention. Particularly useful are enzymatically active groups, such as enzymes, enzyme substrates, coenzymes (see U.S. Pat. Nos. 4,230,797 and 4,238,565), and enzyme inhibitors (see U.S. Pat. No. 4,134,792), fluorescers and chromophores including phycobiliproteins; luminescers such as chemiluminescers and bioluminescers; specifically bindable ligands; and residues comprising radioisotopes such as $H^3$, $S^{35}$, $P^{32}$, $I^{125}$ and $C^{14}$. Such labels are detected on the basis of their own physical properties (e.g., fluorescers, chromophores and radioisotopes) or their reactive or binding properties (e.g., enzymes, substrates, coenzymes and inhibitors). For example, a cofactor-labeled moiety can be detected by adding the enzyme for which the label is a cofactor and a substrate for the enzyme. A hapten or ligand (e.g., biotin) labeled moiety can be detected by adding an antibody or an antibody fragment to the hapten or a protein (e.g., avidin)

which binds the ligand, tagged with a detectable molecule. Such detectable molecule can be a molecule with a measurable physical property (e.g., fluorescence or absorbance) or a participant in an enzyme reaction. For example, one can use an enzyme which acts upon a substrate to generate a product with a measurable physical property. Examples of the latter include, but are not limited to, beta-galactosidase, alkaline phosphatase, papain and peroxidase. Other labels will be evident to one of ordinary skill in the art.

Using these methods, a series of compounds for inhibitory activity on complex formation by N-36 and C-34 was screened. As described hereinbefore, it was found that a phenylazonaphthalene sulfonic acid derivative, designated as "ADJ-1" had the most potent inhibitory activity on the complex formation by N-36 and C-34 and on HIV-1-mediated cell fusion, indicating that it blocks HIV-1-mediated membrane fusion by interfering with the complex formation by the N and C helices of gp41. Interestingly, several other porphyrin derivatives, such as MTCPP, MTSPP and chlorin e6, which were previously shown to interact with the V3 loop of gp120 (Neurath, A. R., N. Strick, P. Haberfield, and S. Jiang, 1992, "Rapid prescreening for antiviral agents against HIV-1 based on their inhibitory activity in site-directed immunoassays. II. Porphyrins reacting with the V3 loop of gp120", *Antiv. Chem. Chemother.*, 31, 55–63; Neurath, A. R., N. Strick, K. Lin, A. K. Debnath, and S. Jiang. 1994, "Tin protoporphyrin IX used in control of heme metabolism in humans effectively inhibits HIV-1 infection", *Antiv. Chem. Chemother.*, 5, 322–330; Debnath, A. K, S. Jiang, and A, R. Neurath, 1995, "Molecular modeling of the V3 loop of the HIV-1 envelope glycoprotein gp 120 reveals a possible binding pocket for porphyrins. In QSAR and molecular modeling: concepts, computational tools and biological applications", Sanz, F., Giraldo, J., Manaut, F., editors, J. R. Prous, Science Publishers, Barcelona. pp. 585–587), also have some inhibitory activity on complex formation by N- and C-peptides, suggesting that they may also interfere with the formation of the gp41 core domain. This action may at least partly contribute to their anti-HIV-1 activity. ATA also inhibits HIV-1 infection via multiple mechanisms, i.e., inhibiting reverse transcriptase activity (Balzarini, J., H, Mitsuya, E. De Clercq, and S. Broder, 1986, "Aunintricarboxylic acid and Evans Blue represent two different classes of anionic compounds which selectively inhibit the cytopathogenicity of human T-cell lymphotropic virus type III/lymphadenopathy-associated virus", *Biochem. Biophys. Res. Commun.*, 136–6471), blocking gp120 binding to CD4 (Schols, D., M. Baba, R. Pauwels, I. Desmyter, and F. De Clercq, 1989, "Specific interaction of aurintricarboxylic acid with the human immunodeficiency virus/CD4 cell receptor", *Proc. Natl. Acad. Sci. USA*, 86:3322–3326) and interacting with the V3 loop of gp120 (Neurath, A. R., P. Haberfield, B. Joshi, L. K. Hewlett, N. Strick, and S. Jiang, 1991, "Rapid prescreening for antiviral agents against HIV-1 based on their inhibitory activity in site-directed immunoassays. 1. The V3 loop of gp120 as target", *Antiv. Chem. Chemother.*, 2, 303–312), but not blocking the complex formation by N- and C-peptides. Thus, the method described herein can distinguish the anti-HIV-1 agents targeting the gp41 core domain from those having different targets. Although several antiviral agents have strong inhibitory activity on HIV-1-induced membrane fusion, they are not targeted to gp41. 3HP-β-LG inhibits the binding of gp120 to CD4 receptor (Neurath et al., 1996, *Nature Med.*, 2, 230–234) and the peptide T-22 ([Tyr5,12, Lys7]-polyphemusin II) is a potent inhibitor of HIV-1 binding to CXCR4 (Murakami, T., T. Nakajima, Y. Koyanagi, K. Tachibana, N. Fujii, H. Tamamura, N. Yoshida, M. Waki, A. Matsumoto, O. Yoshie, T. Kishimoto, N. Yamamoto, and T. Nagasawa, 1997, "A small molecule CXCR4 inhibitor that blocks T cell linetropic HIV-1 infection", *J Exp. Med.*, 198, 1389–1393), but they do not inhibit the complex formation by N- and C-peptides.

The position might be taken that ADJ-J1, selected by a sandwich ELISA, may not block the complex formation by N- and C-peptides, but instead block NC-1 binding to the complex, either due to its association with MAb NC-1 or with the N36/C34 complex. The first possibility was excluded, since the antibody-coated wells of the plastic plates were extensively washed after addition of the mixture of N36, ADS-J1 and C34 and before. addition of MAb NC-1, excluding the presence of unbound ADS-J1, which could bind to MAb NC-1. To determine whether or not ADS-J1 binds to the surface of the N36/C34 complex and blocks NC-1 binding, a control experiment was conducted in which the complex In was preformed by mixing N36 and C34 at equimolar concentrations and captured to the wells of plastic plates coated with rabbit antibody directed against N36/C34 complex. Then, the binding of MAb NC-1 to the preformed complex in the presence of ADS-J1 at different concentrations was determined. ADS-J1 was unable to block the binding of NC-1 to the preformed N36/C34 complex. This result indicates that inhibition of NC-1 binding by ADS-J1 is due to its inhibition of complex formation by N- and C-peptides, rather than to the inhibition of antibody binding to the preformed complexes consisting of N- and C-peptides.

Since the residues located at the interaction sites in both the NHR and CHR regions of gp41 are highly conserved, the antiviral agents targeted to the gp41 core are considered to have broader specificity against infection by HIV strains than those targeted to gp120.

Compounds for providing inhibitory activity against HIV-1 infection include compounds of the following formula (I) and formula (II):

Compounds of Formula (I)

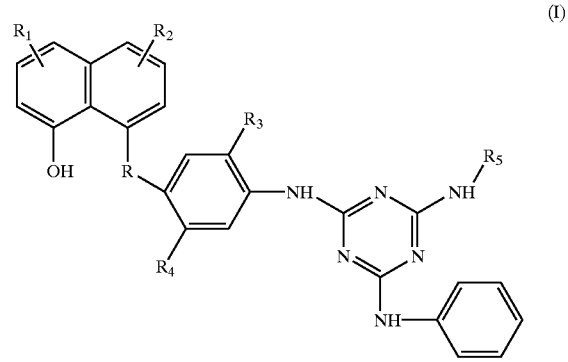

(I)

wherein R=—N=N—, —CONH—, or —SO$_2$NH—; R$_1$=—SO$_3$H, —COOH; R$_2$=—SO$_3$H, —COOH; R$_3$=—O—C$_1$–C$_{10}$ alkyl such as —OCH$_3$ or —OC$_2$H$_5$; or S—C$_1$–C$_{10}$ alkyl such as —SCH$_3$, —SC$_2$H$_5$; R$_4$=—H, hydroxy, C$_1$–C$_{10}$ alkoxy, carboxylic acid group, unsubstituted or substituted C$_1$–C$_{10}$ alkyl group (substituted with a halogen, hydroxy, C$_1$–C$_{10}$ alkoxy or carboxylic acid group), such as —CH$_3$ or —C$_2$H$_5$; R$_5$=unsubstituted or substituted aryl or unsubstituted or substituted naphthyl, wherein the substituent is a halogen, hydroxy, C$_1$–C$_{10}$ alkyl, sulfonic acid group or carboxylic acid group or R$_5$ is an unsubstituted or substituted aryl azo, wherein one or more rings thereof are substituted with a $C_1$–$C_{10}$ alkyl, halogen (such as chlorine or fluorine), hydroxy, $C_1$–$C_{10}$ alkoxy, a sulfonic acid group or a carboxylic acid group, such as

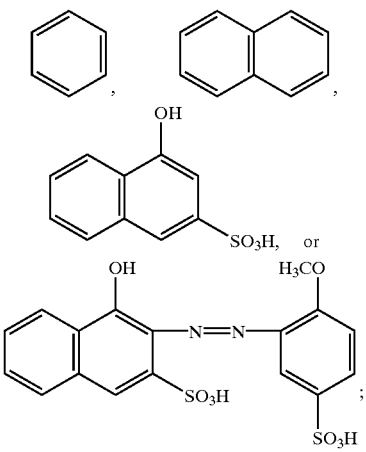

Compounds of formula (II)

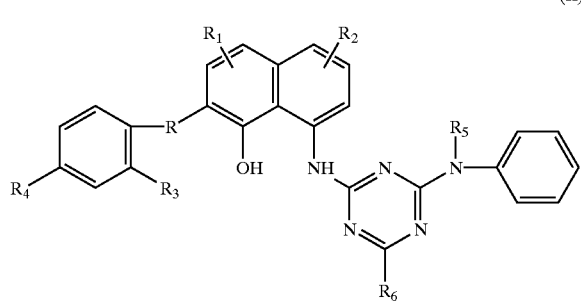

wherein R=—N═N—, —CONH—, —$SO_2NH$—; $R_1$=—$SO_3H$, —COOH; $R_2$=—$SO_3H$, —COOH; $R_3$=—H, —$SO_3H$, —COOH; $R_4$=—H, a halogen, hydroxy, $C_1$–$C_{10}$ alkoxy, carboxylic acid group, unsubstituted or substituted $C_1$–$C_{10}$ alkyl group (substituted with a halogen, hydroxy, $C_1$–$C_{10}$ alkoxy or carboxylic acid group), such as —$CH_3$ or —$C_2H_5$; $R_5$=—H, or unsubstituted or substituted $C_1$–$C_{10}$ alkyl (substituted with a halogen, hydroxy, $C_1$–$C_{10}$ alkoxy or carboxylic acid group), such as —$CH_3$ or —$C_2H_5$; $R_6$=a halogen such as chlorine or bromine or an unsubstituted or substituted arylamine group (substituted with a halogen, hydroxy, $C_1$–$C_{10}$ alkoxy, carboxylic acid group or a sulfonic acid group), such as —$NHC_6H_5$.

Also pharmaceutically acceptable salts of the compounds of formula (I) and formula (II) can be employed. Non-limiting examples of such pharmaceutical acceptable salts include sodium salts and potassium salts.

Specifically, using ELISA methods, in combination with a computer-aided molecular docking technique and HIV-1 inhibition assays, the following small molecule compounds were found to have inhibitory activity against HIV-1 infection: 7-[6-phenylamino-4-[4-[(3,5-disulfo-8-hydroxynaphthyl)azo]-2-methoxy-5-methylphenylamino]-1,3,5,triazine-2-yl]-4-hydroxy-3-[(2-methoxy-5-sulfophenyl)azo]-2-naphthalene sulfonic acid ("ADS-J1") (see TABLE 1) and 5-[(4-chloro-6-phenylamino-1,3,5-triazine-2-yl)-amino]-4-hydroxy-3-[(4-methyl-6-sulfophenyl)azo]-2,7-naphthalene disulfonic acid ("ADS-J2") (see TABLE 1).

The present invention also provides an antiviral pharmaceutically active compound having a negatively charged group, such as $SO_3$— or COO—, which forms a salt bridge with a positively charged residue such as lysine or arginine, at a specified position in the HIV-1 gp41, the salt bridge providing anti-HIV-1 activity. The positively charged residue such as lysine or arginine can be at a position in gp41 of a HIV-1 isolate corresponding to Lys 574 in gp41 of the HIV-1 isolate HXB2.

It is preferred that the pharmaceutically active compound for use in the present invention be formulated into pharmaceutical preparations. Such preparations are composed of one or more of the compounds for use in the present invention in association with a pharmaceutically acceptable carrier. *Remington's Pharmaceutical Sciences,* 75th Edition, A. R. Gennaro, editor (Mack Publishing Company, 1985), discloses typical carriers and methods of preparation.

The pharmaceutically active compound described for use in the present invention can be administered systemically or typically to humans. Non-limiting modes of administration include oral, rectal, buccal, sub-lingual, vaginal, nasal and parenteral (i.e., intramuscular, intravenous and subcutaneous). Generally it will be found that when the pharmaceutically active compound is administered orally, a larger quantity of the pharmaceutically active compound is required to produce the same effect as the smaller quantity given parenterally. In accordance with good clinical practice, it is preferred to administer the pharmaceutically active compound at a concentration level that will produce the desired effects without causing any harmful or untoward side effects.

The pharmaceutically active compound is preferably administered as a pharmaceutical composition comprised of an effective anti-HIV-1 amount of the pharmaceutically active compound or a pharmaceutically acceptable salt thereof or a pharmaceutically acceptable ester thereof and a pharmaceutically acceptable carrier. Pharmaceutical compositions for effecting such treatment will contain a major or minor amount, e.g., from 95 to 0.5% of the pharmaceutically active compound in combination with a pharmaceutical carrier, the carrier comprising one or more solid, semi-solid, or liquid diluents, fillers and formulation adjuvants which are non-toxic inert and pharmaceutically acceptable. Such pharmaceutical compositions are preferable in dosage unit form, i.e., physically discrete units containing a predetermined amount of the drug corresponding to a fraction or multiple of the dose which is calculated to produce the desired therapeutic response. Other therapeutic agents can also be present.

Pharmaceutical compositions providing from about 1 to 50 mg of the pharmaceutically active compound per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g., syrup, acacia, gelatin, sorbitol, tragacanth or polyvinylpyrrolidone), fillers (e.g., lactose, sugar, corn starch, calcium phosphate, sorbitol or glycine), lubricants (e.g., magnesium stearate, talc, polyethylene glycol or silica), disintegrants (e.g., starch) and wetting agents (e.g., sodium lauryl sulfate). Solutions or suspensions of the pharmaceutically active compound with conventional pharmaceutical vehicles are employed for parenteral compositions, such as an aqueous solution for intravenous injection or an oily suspension for intramuscular injection. Such compositions having the desired clarity, stability and adaptability for parenteral use are obtained by dissolving from 0.1% to 10% by weight of the pharmaceutically active compound in water or a vehicle comprising a polyhydric aliphatic alcohol, such as glycerine, propylene glycol and polyethylene glycol or mixtures thereof. The polyethylene glycols comprise a mixture of non-volatile, usually liquid, polyethylene glycols which are soluble in both water and organic liquids and have molecular weights from about 200 to 1500.

For clinical applications, the dosage and dosage regimen in each case should be carefully adjusted, utilizing sound professional judgment and consideration of the age, weight and condition of the recipient, the route of administration and the nature and gravity of the HIV infection. The dosage may vary based on the medical status of the recipient, e.g., dosages may have to be decreased in cases of impaired metabolism or increased in cases of enhanced metabolism. In some instances, a sufficient therapeutic or prophylactic effect can be obtained at lower doses, while in others, larger doses will be required.

The amount of active compound administered should be sufficient to maintain an effective blood serum concentration of about 0.005 mg/ml to 0.01 mg/ml.

Additionally, the active compound for use in the present invention can be administered in conjunction with other anti-HIV drugs such as AZT.

The present invention will now be described with respect of the following non-limiting examples.

EXAMPLES

Example 1

Monoclonal Antibodies Directed Against the Six-Helix Core of gp41

Example 1A

Generation of Monoclonal Antibodies by Immunizing Mice with a Complex Containing N- and C-Peptides To generate mouse monoclonal antibodies against the highly conserved core structure of gp41, three BALB/c mice were primarily immunized intraperitoneally with 100 µg of recombinant N36(L6)C34 polypeptide formulated with Freund's complete adjuvant. N36(L6)C34 is a stable subdomain consisting of two peptides, N-36 and C-34, connected by a six-residue hydrophilic linker. The structure and characterization of the model polypeptide are described in Lu et al., *Natl. Struct. Biol.*, 2, 1075–1082, 1995; and Lu et al., *J. Biomol. Struct. Dyn.*, 15, 465–471, 1997.

The secondary immunizations were carried out intraperitoneally at 3-week intervals with the same amount of antigen combined with Freund's incomplete adjuvant. Murine sera were assayed 10 days later or reactivities specific to the N36(L6)C34 antigen by an enzyme-linked immunosorbent assay (ELISA) as described below. One mouse having a strong serum antibody response to the antigen received a final intravenous booster via the tail. Four days later, the mouse was bled and sacrificed by cervical dislocation. The splenocytes from this mouse were fused with SP2/0 myeloma cells and cultured in hypoxanthine-aminopterin-thymidine medium in a 96-well plate. After incubation for 10 days, the culture supernatants were collected and screened by ELISA for antibodies to N36(L6)C34. After the first screening, 4 positive wells were selected for further cloning. Finally, one clone of hybridoma cells, designated NC-1, that continuously secreted antibody at high concentrations was established. Immunoglobulin G (IgG) was purified from the ascites fluid obtained from mice injected with NC-1 hybridoma cells and was used for the immunological studies. The isotope of this monoclonal antibody is IgG2a.

The ELISA was carried out as described in Neurath, A. R., N. Strick and S. Jiang, 1992, "Synthetic peptides and anti-peptide antibodies as probes to study inter-domain interactions involved in virus assembly: the envelope of the human immunodeficiency virus (HIV-1)", *Virology.* 188, 1–13.

A peptide or protein antigen dissolved in 0.1 M Tris (pH 8.8) was used to coat wells of a 96-well polystyrene plate (Immulon II; Dynatech Laboratories, Inc., Chantilly, Va.) and blocked with a blocking buffer (phosphate-buffered saline plus 5% horse serum). Mouse sera and culture supernatants containing antibodies or purified IgG were added to the wells at various concentrations. Then, biotin-labeled goat anti-mouse IgG (Boehringer Mannheim, Indianapolis, Ind.), streptavidin-labeled horseradish peroxidase (Zymed, San Francisco, Calif.), and the substrate 3,3',5,5'-tetramethylbenzidine (Sigma Chemical Co., St. Louis, Mo.) were added sequentially. The optical density at 450 nm ($OD_{450}$) was read in an ELISA reader (Dynatech Laboratories, Inc.). Each sample was tested in triplicate.

Example 1B

Specific Recognition of Conformational Epitopes on the Six-Helix Core of gp41 by NC-1

Figure 4:
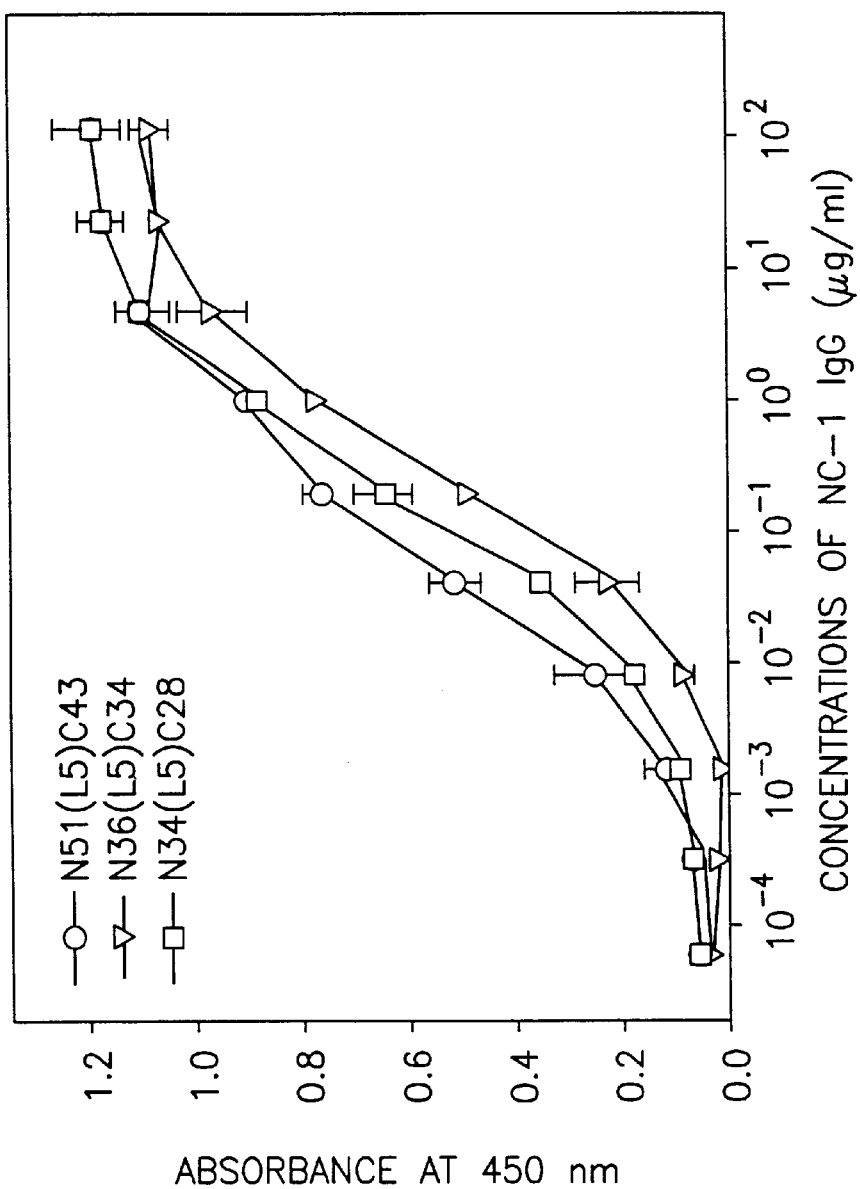
FIG. 4 is a graph showing the binding of NC-1 to model polypeptides containing N- and C-peptides.

Previous studies have shown that the model polypeptide N51(L6)C43 represents the larger domain of gp41, while the N34(L6)C28 polypeptide folds into a minimal six-helix core. To examine whether the NC-1 MAb is capable of binding to the gp41 core, its reactivity to the N36(L6)C34 immunogen and the N51(L6)C43 and N34(L6)C28 polypeptides were examined by ELISA. Each of the N51(L6)C43, N36(L6)C34, and N34(L6)C28 polypeptides (approximately 1 µM) were used to coat wells of a microplate. As shown in FIG. 4, the antibody-binding properties of these polypeptides are similar, with dilution endpoints of 2.0 ng of IgG/ml for N51(L6)C43, 6.1 ng of IgG/ml for N36(L6)C34, and 2.3 ng of IgG/ml for N34(L6)C28.

Protein dissection studies demonstrated that, in isolation, the N-36 peptide is predominantly aggregated, while the C-34 peptide is unfolded; upon mixing, these peptides form a stable trimer of heterodimers (FIG. 3). To test whether the NC-1 MAb recognizes conformational and/or sequential epitopes, 96-well polystyrene plates were coated with the isolated N-36 and C-34 peptides and an equimolar mixture of the N-36 and N-34 peptides. Then the 96 well polystyrene plates were reacted with the purified NC-1 IgG (10 µg/ml); the following controls were included: wells coated with unrelated peptides derived from the HIV-1$_{IIIB}$ V3 loop ($OD_{450}$ [mean±standard deviation]=0.052±0.018) and from the immunodominant region of gp41 (residues 572 to 598) ($OD_{450}$=0.061±0.040) and wells with the N-36 and C-34 complex reacted with normal mouse IgG (10 µg/ml) ($OD_{450}$=0.132±0.033). As measured by ELISA, NC-1 exhibited a strong reactivity to the N-36 and C-34 complex (FIG. 5A). In contrast, the isolated N-36 and C-34 peptides failed to bind the antibody (FIG. 5A). These results indicate that the NC-1 MAb recognizes conformational epitopes on the gp41 core.

Figure 5B:
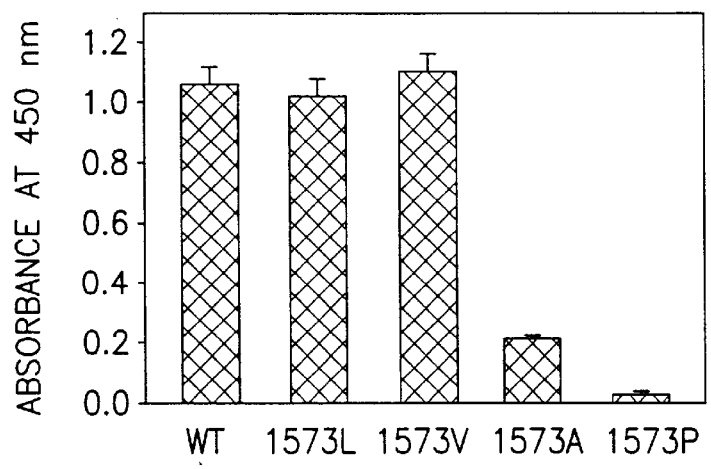

Single-point mutations within the highly-conserved N-terminal heptad repeat region abolish the ability of gp120 and gp41 to mediate membrane fusion. Studies of model peptides demonstrated that these mutations also can disrupt formation of the minimal N34(L6)C28 core subdomain. It was of interest to see whether NC-1 reactivity to the N34 (L6)C28 subdomain was abolished by these fusion-defective mutations. Single-point mutations (I573L, I573V, I573A, and I573P) were introduced into pN34/C28-L6 by oligonucleotide-directed mutagenesis, and the recombinant proteins were expressed and purified as previously described. As shown in FIG. 5B, the mutant N34(L6)C28 peptides were conserved mutations (I573L and I573V) had binding activities for NC-1 similar to that of the wild-type molecule, but those with the fusion-defective mutations (I573P and I573A) did not bind to the NC-1 MAb. These results are strong evidence that NC-1 specifically recognizes the six-helix core structure of the gp41 molecule.

Figure 5C:
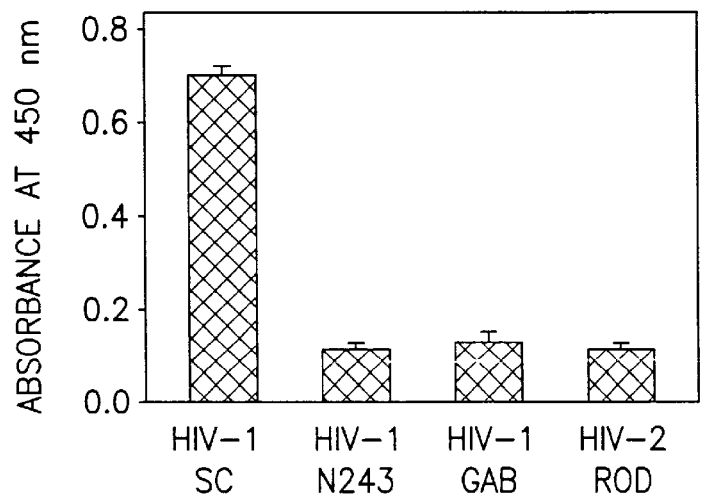

To determine whether MAb NC-1 has broad reactivity, the binding of NC-1 to the complexes reconstituted with N-36 and C-peptides derived from the transmembrane glycoprotein sequences of HIV-1$_{SC}$ (clade B), HIV-1$_{N243}$ (clade E), HIV-1$_{GAB}$ (clade O), and HIV-2$_{ROD}$ were tested. As shown in FIG. 5C, NC-1 strongly bound to the complex formed by N-36 and the C-peptide from HIV-1$_{SC}$, which belongs to the same clade as HIV-1$_{IIIB}$, but not to those formed by N-36 and C-peptides from other HIV-1 and HIV-2 strains. These results indicate that NC-1 recognizes the gp41 core domain derived from strains closely related to HIV-1$_{IIIB}$. A recent study has demonstrated that N-peptide from HIV-1 formed a heterotypic complex with C-peptide from simian immunodeficiency virus (Malashkevich, V., D. C. Chan, C. T. Chutkowski, and P. S. Kim, 1998, "Crystal structure of the simian immunodeficiency virus (SIV) gp41 core: conserved helical interactions underlie the broad inhibitory activity of gp41 peptides", *Proc. Natl. Acad. Sci. USA*, 95, 9134–9139). It is likely that the N-peptide from HIV-1$_{IIIB}$ and C-peptides from HIV-2 and other HIV-1 strains may also form six-helix core domains. Therefore, the inability of NC-1 to bind to these heterotypic complexes is probably due to the variation of the residues on the surface of the helical core domain that participate in the formation of discontinuous epitopes for MAb NC-1.

Example 1C

NC-1 Reacts with the Oligomeric Forms of gp41

The gp120 and gp41 complex exists as either trimers or tetramers on the surfaces of virions and HIV-1 infected cells (Earl, P. L., R. W. Doms, and B. Moss, 1990, "Oligomeric structure of the human immunodeficiency virus type 1 envelope glycoprotein", *Proc. Natl. Acad. Sci. USA*, 87, 648–652; Pinter, A., W. J. Honnen, S. A. Tilley, C. Bona, H. Zaghouani, M. K. Gorny, and S. Zolla-Pazner, 1989, "Oligomeric structure of gp41, the transmembrane protein of human immunodeficiency virus type 1", *J. Virol.*, 63, 2674–2679; Schawaller, M., G. E. Smith, J. J. Skehel, and D. W. Wiley, 1989, "Studies with crosslinking reagents on the oligomeric structure of the env glycoprotein of HIV", *Virology*, 172, 367–369; Weiss, C. D., J. A. Levy, and J. M. White, 1990, "Oligomeric organization of gp120 on infectious human immunodeficiency virus type 1 particles", *J. Virol.*, 64, 5674–5677). The reactivity of the NC-1 MAb to viral gp41 was examined by Western blot assay.

Strips with electrophoretically separated HIV-1$_{IIIB}$ and HIV-2$_{G122B1}$ proteins were obtained from Cambridge Biotech, Worcester, Mass. The attachment of the MAb NC-1 IgG was detected with biotinylated goat anti-mouse IgG antibody (Boehringer Mannheim) followed by strept-avidin-conjugated horseradish peroxidase and the substrate from the Western blot kit. Human MAb 2F5, which recognizes an epitope encompassing residues 662 to 667 (ELDKWA) (Muster, T., R. Guinea, A. Trkola, M. Purtscher, A. Klima, F. Steindl, P. Palese, and H. Katinger, 1994, "Cross-neutralizing activity against divergent human immunodeficiency virus type 1 isolates induced by the gp41 sequence ELDKWAS", *J. Virol.*, 68, 4031–4034), was purchased from Polymun Scientific Immunbiologische Forschung GmbH, Vienna, Austria, and was used as a control.

Figure 6:
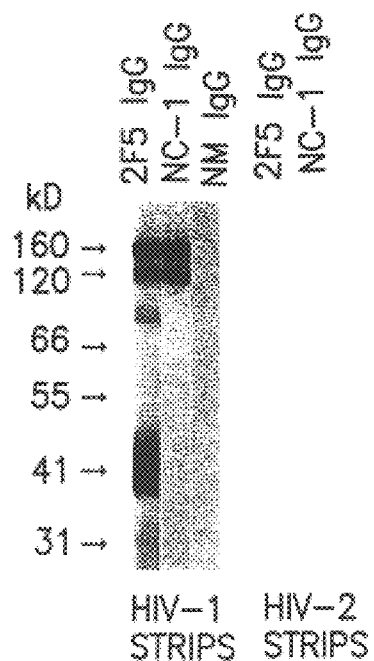
FIG. 6 depicts a Western blot which shows the detection of antibody binding to different forms of transmembrane proteins from HIV-1 and HIV-2.

The binding of the purified NC-1 IgG (10 μg/ml) to the electrophoretically separated protein from HIV-1$_{IIIB}$ and HIV-2$_{GB122B1}$ was tested by Western blotting. Normal mouse (NM) IgG and MAb 2F5 IgG were used as controls. As shown in FIG. 6, NC-1 binds to two bands with molecular masses of about 120 and 160 kDa in the HIV-1 strip. Since NC-1 did not react with gp120 and gp160 (MicroGenesis, Meriden, Conn.) in a separate Western blot assay (data not shown), it was assumed that these two bands are probably gp41 trimers and tetramers.

MAb 2F5 bound to bands in the HIV-1 strip with molecular masses of about 40, 80, 120, and 160 kDa, which correspond to gp41 monomers, dimers, trimers, and tetramers, respectively, consistent with previous observation (Neurath, A. R., N. Strick, K. Lin, and S. Jiang, 1995, "Multifaceted consequences of anti-gp41 monoclonal antibody 2F5 binding to HIV-1 virions", *AIDS Res. Hum. Retroviruses*, 11, 687–696). By contrast, neither MAb NC-1 nor 2F5 reacted with any protein in the HIV-2 strip (FIG. 6). These results indicate that the NC-1 MAb can recognize the discontinuous epitopes on the oligomers of HIV-1$_{IIIB}$ gp41, but cannot react with the transmembrane glycoprotein of an HIV-2 strain.

Example 1D

Binding of NC-1 to gp41 Upon Addition of sCD4

Numerous studies have led to the proposal that the binding of gp120 to the CD4 receptor triggers a major conformational change in gp41 that induces fusion of viral membranes with target cell membranes. Evidence for this conformational change includes soluble-CD4(sCD4)-induced dissociation (shedding) of gp120 from the viral surface (Hart, T. K., R. Kirsh, H. Ellens, R. W. Sweet, D. M. Lambert, S. R. Petteway, Jr., J. Leary, and P. J. Bugelski, 1991, "Binding of soluble CD4 proteins to human immunodeficiency virus type 1 and infected cells induces release of envelope glycoprotein gp120", *Proc. Natl. Acad. Sci. USA*, 88, 2189–2193; Sullivan, N., Y. Sun, J. Li, W. Hofmann, and J. Sodroski, 1995, "Replicative function and neutralization sensitivity of envelope glycoproteins from primary and T-cell line-passaged human immunodeficiency virus type 1 isolates", *J. Virol.*, 69, 4413–4422) and an increased exposure of epitopes on gp41 (Sattentau, Q. J., and J. P. Moore, 1991, "Conformational changes induced in the human immunodeficiency virus envelope glycoprotein by soluble CD4 binding", *J. Exp. Med.*, 174, 407–415). Several lines or evidence strongly suggest that the six-helix structure within the gp41 ectodomain represents the fusion-active conformation. It was surmised that the NC-1 MAb would bind to gp41 only after its conformational change to the fusion-active state.

Figure 7A:
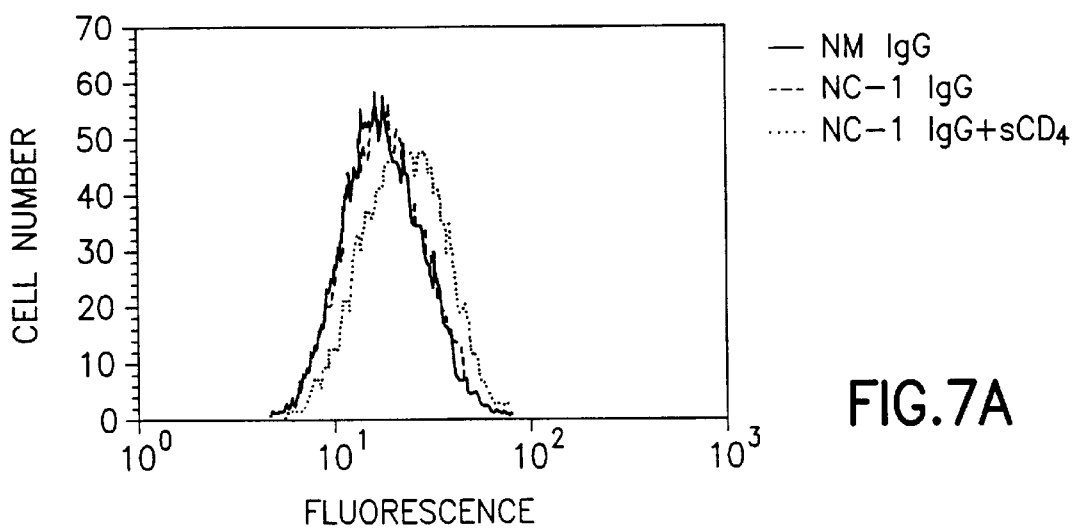
FIGS. 7A to 7C are graphs which show the binding of MAb NC-1 to transmembrane glycoproteins expressed on HIV-infected cells by a flow cytometric analysis using normal mouse (NM) IgG as a control.
Figure 7B:
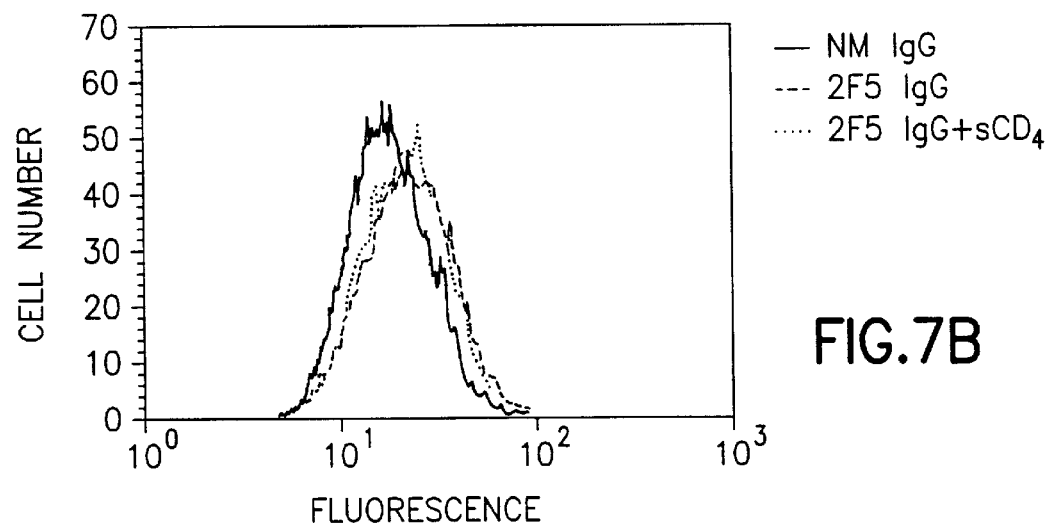
Figure 7C:
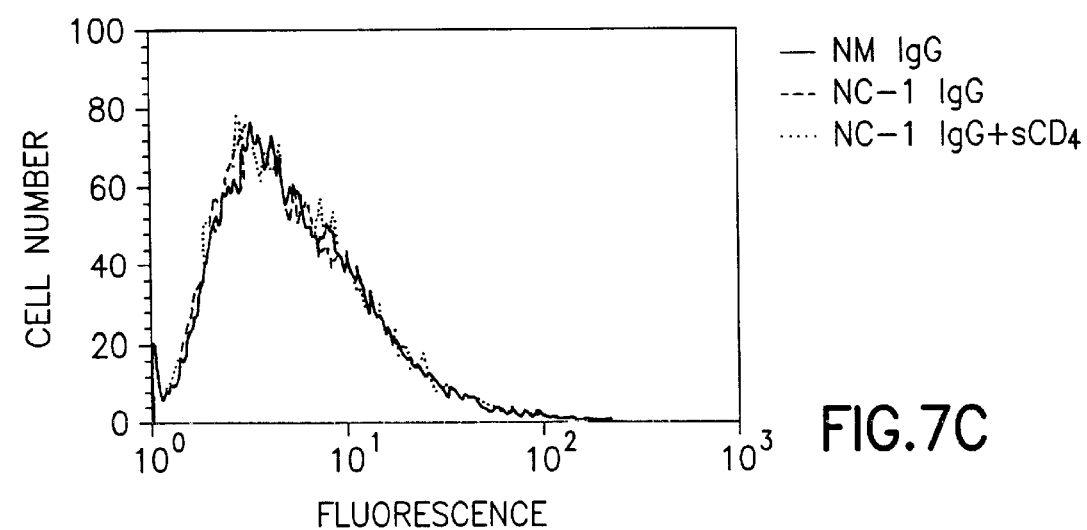

To test this hypothesis, flow cytometry was used to analyze the binding of the NC-1 MAb to HIV-infected cells. The NC-1 IgG was incubated with HIV-1$_{IIIB}$-infected H9 cells and HIV-2$_{ROD}$-infected U937 cells in the presence or absence of sCD4 (immunoDiagnostics, Bedford, Mass.) at 37° C. for 30 minutes, MAb 2F5 IgG was used as a control. The cells were incubated with biotinylated goat anti-mouse IgF (or anti-human IgG for 2F5) and streptavidin-conjugated fluorescein isothiocyanate (Zymed) sequentially. After extensive washes, the cells were fixed with 1% formaldehyde and analyzed by flow cytometry. Remarkably, the binding of NC-1 to the surfaces of HIV-1-infected calls was detected only after addition of sCD4 (FIG. 7A). In contrast, the 2F5 MAb had similar reactivities. with HIV-1 infected cells in the presence and absence of sCD4 (FIG. 7B). NC-1 did not bind to HIV-2-infected cells, even in the presence of sCD4 (FIG. 7C). It was concluded that the NC-1 MAb recognizes conformation-specific epitopes on fusion-active HIV-1 gp41.

Example 2

Screening Assay for Antiviral Compounds Targeted to the HIV-1 gp41 Core Structure Cells Peptides Peptides were synthesized by a standard solid-phase FMOC method. The N-termini of the peptides were acetylated and their C-termini were amidated. The peptides were purified to homogeneity by high-performance liquid chromatography (HPLC). The identity of the purified peptides was confirmed by laser desorption mass spectrometry (PerSeptive Biosystems).

Chemical Compounds

The following porphyrin derivatives were obtained from Porphyrin Products, Inc. (Logan, Utah): meso-tetra(4-carboxyphenyl)porphyrin (MTCPP), meso-tetra(4-sulphonatophenyl)porphyrin (MTSPP), uroporphyrin I (UP-I), protoporphyrin IX (PP-IX), tin protoporphyrin IX (Sn-PP-IX), aluminum phthalocyanine tetrasulfionate (AL-PcS) and chlorin e6. A 7-[6-phenylamino-4-[4-[(8-hydroxynaphthyl)azo]phenylamino]-1,3,5-triazine-2-yl]-4-hydroxy-3-phenylazo-2-naphthalene sulfonic acid derivative, designated as "ADS-J1", (see TABLE 1 hereinafter) which was purchased from ComGenex, Inc. (Budapest, Hungary), was also used.

Hemin and aurintricarboxylic acid (ATA) were purchased from Sigma (St Louis, Mo.). Azidothymidine (AZT) was obtained from Boehringer Mannheim (Indianapolis, Ind.). 3-hydroxyphthalic anhydride modified β-lactoglobulin (3HP-β-LG) was prepared as described in Neurath, A. R., S. Jiang, N. Strick, K. Lin, Y.-Y. Li, and A. K. Debnath, 1996, Bovine β-lactoglobulin modified by 3-hydroxyphthalic anhydride blocks the CD4 cell receptors for HIV-1, Nature Med., 2, 230–234.

Polyclonal and Monoclonal Antibodies

For generation of polyclonal antibodies (PAbs), NZW rabbits were immunized with 200 μg of the respective peptides in combination with complete Freund's adjuvant and boosted with the same amount of immunogens mixed with incomplete Freund's adjuvant at intervals of two weeks. Ten weeks after the initial immunization, blood was collected by cardiac puncture. Antisera were stored at 4° C. until use. The mouse MAb NC-1 directed against the recombinant N36(L6)C34 polypeptide was used. Rabbit and mouse IgG were purified using protein-A kits (Pierce, Rockford, Ill.).

ELISA

The ELISA assay was carried out as described in Neurath, A. R., N. Strick, and S. Jiang, 1992, "Synthetic peptides and anti-peptide antibodies as probes to study inter-domain interactions involved in virus assemble the envelope of the human immunodeficiency virus (HIV-1)", Virology, 188, 1–13.

Peptides dissolved in 0.1 M Tris (pH 8.8) were used to coat a 96-well polystyrene plate (Immulon II, Dynatech Laboratories, Inc., Chantilly, Va.) which was then blocked with phosphate-buffered saline (PBS) containing 5% horse serum and 0.05% TWEEN-20. Antiserum or monoclonal antibody was added to the wells at indicated concentrations. Then, biotin labeled goat-anti-mouse IgG (Boehringer Mannheim), streptavidin-labeled horseradish peroxidase (Zymed, San Francisco, Calif.), and the substrate 3,3',5, 5'tetramethylbenzidine (Sigma Chemical Co., St. Louis, Mo.) were added sequentially. The absorbance at 450 nm ($A_{450}$ was read in an ELISA reader (Dynatech Laboratories, Inc., Chantilly, Va.). Each sample was tested in triplicate.

For detection of peptide complexes, a direct and a sandwich ELISA were used. In the direct ELISA, the N- and C-peptides were mixed at equimolar concentration in PBS and diluted in coating buffer. Then, the peptide complexes were directly coated onto the wells of microplate. In the sandwich ELISA, the plate was coated with IgG (10 μg/ml) purified from rabbit antisera directed against N36(L6)C34, followed by the addition of the peptide complexes formed by mixing N- and C-peptides in PBS in equimolar concentrations. To screen for antiviral agents, compounds were pre-incubated with N-peptides at 37° C. for 30 minutes before mixing with the C-peptides. The binding of the peptide complexes to the antibodies was then detected as described above.

The percentage of inhibition by the compounds of the binding of NC-1 to the peptide complexes was calculated as described in Jiang, S., K. Lin, and A. R. Neurath, 1991, "Enhancement of human immunodeficiency virus type-1 (HIV-1) infection by antisera to peptides from the envelope glycoproteins gp120/gp41", J. Exp. Med., 174, 1557–1563.

Dot Blot

The binding of antibodies to peptides and peptide complexes was assayed by a dot blot. 5 μl of individual peptides or peptide complexes (2 μM in PBS) were added onto a nitrocellulose membrane (Schleicher & Schuell, Keene, N.H.). The membrane was blocked with a blocking buffer (PBS containing 3% nonfat dry milk and 0.05% TWEEN 20) at room temperature for 30 minutes and was cut into strips. The strips were then incubated with PAb or MAb at indicated concentrations at 37° C. for 1 hour. After extensive washes, the strips were incubated with biotin-labeled goat-anti-rabbit or antimouse IgG (Boehringer Mannheim), followed by incubation with streptavidin-conjugated horseradish peroxidase (Zymed) and a chemiluminescence detection solution (Amersham Life Science, Buckinghamshire, England) sequentially. The strips were then exposed to an autoradiographic film.

HIV-1-Mediated Cell Fusion

A dye transfer assay was used for detection of HIV-1-mediated cell fusion as described in Jiang et al., Nature, 365, 113 (1993). H9/HIV-1$_{IIIB}$ cells were labeled with a fluorescent reagent, 2',7'-bis-(2-carboxyethyl)-5-and-6-carboxyfluorescein acetoxyethyl ester (BCECF-AM), (Molecular Probes, Inc., Eugene, Oreg.) and incubated with MT-2 cells (ratio=1:10) in a 96-well plate at 37° C. for 2 hours in the presence or absence of peptides or compounds tested. The fused and unfused BCECF-labeled HIV-1 infected cells were counted under an inverted fluorescence microscope (Zeiss, Germany) with an eyepiece micrometer discs. The percentage of inhibition of cell fusion was calculated as described in Jiang et al., 1993, Nature, 365, 113.

Results

Binding of the PAbs and MAb to Peptides and Peptide Complexes

Figure 9:
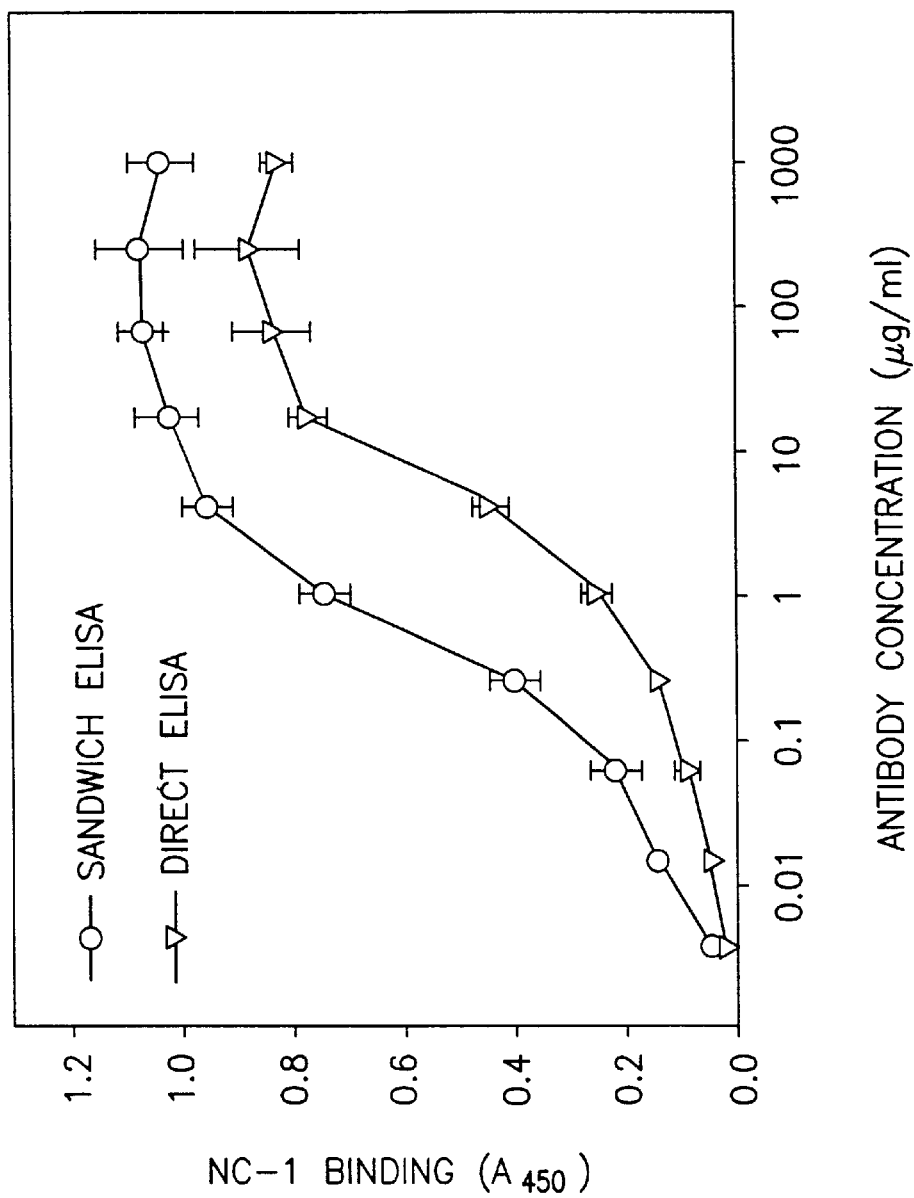
FIG. 9 is a graph showing the comparison of sensitivity of the direct ELISA and sandwich ELISA for the detection of NC-1 binding to the N-36/C-34 complex. In the sandwich ELISA, the complex was captured by a polyclonal antibody directed against N36(L6)C34, rather than being directly coated on a plate as in the direct ELISA.

The binding activity of the PAbs directed against N-36, C-34 and N36(L6)C34, and of MAb NC-1 to the individual peptides N-36 and C-34 and to peptide complexes N-36/C-34 and N36(L6)C34 was compared using a dot blot assay. As shown in FIG. 8, polyclonal antibodies directed against the individual peptides reacted with the corresponding peptides, e.g., polyclonal antibodies against N-36 bound only to N-36, not to C-34, and vice versa. Polyclonal antibodies to both of N-36 and C-34 reacted with the complexes N-36/C-34 and N36(L6)C34. The polyclonal antibodies directed against N36(L6)C34 bound to all the individual peptides and the peptide complexes. MAb NC-1 did not react with the individual peptides N-36 and C-34, but strongly bound to the complexes N-36/C-34 and N36(L6)C34. These results indicate that MAb NC-1, unlike polyclonal antibodies, specifically recognizes discontinuous epitopes on the complexes formed by the N- and C-peptides. Similar results were obtained by ELISA (data not shown). Previously, a direct ELISA was used, in which the peptide complex N-36/C-34 was directly coated onto plates. A sandwich ELISA was established by capturing the N-36/C-34 complex with IgG purified from rabbit antisera directed against N36(L6)C34. The results indicate that the sandwich ELISA is much more sensitive (about 30 fold) than the direct ELISA for determining NCI binding to the N-36/C-34 complex (FIG. 9), suggesting that direct coating may alter the conformational structure or accessibility of epitopes on the N-36/C-34 complex. Therefore, the sandwich ELISA can be used for the detection of the binding of antibodies to the N-36/C-34 complex.

Peptides Derived Only from the gp41 NHR and CHR Regions Form Complexes Detectable by NC-1

To determine the specificity of the peptide interaction, synthetic peptides derived from the HIV-1 gp120/gp41 were mixed with the peptides N-36 and C34, respectively, and the binding of MAb NC-1 to the captured peptides was tested by ELISA. As shown in FIG. 10, only the peptide SJ-2176 which corresponds to the sequence 630–659 (Jiang, S. and K. Lin, 1995, "Effect of modification of a peptide derived from the HIV-1 gp41 sequences on the antiviral activity", Peptide Res., 8, 345–348) and overlaps with C-34 (see FIG. 1) formed a detectable complex with N36. With respect of FIG. 10, peptides derived from the sequences of gp120/gp41 were mixed with N-36 or C-34 at equimolar concentrations (2 $\mu$M) and added to the wells coated with rabbit anti-N36 (L6)C34 antibody. The binding of NC-1 IgG (5 $\mu$g/ml) to the peptide complexes was detected by the sandwich ELISA. Another peptide, DP-107 which is derived from the gp41 NHR region (see FIG. 1), interacted with the peptide C-34. There may be some other peptide interactions, but they may not result in the formation of the six-stranded α-helical complexes and are unlikely to be detected by monoclonal antibody NC-1. These results indicate that the interaction between only the N- and C-peptides can result in the unique six-helix complexes which are detectable by monoclonal antibody NC-1.

Figure 11:
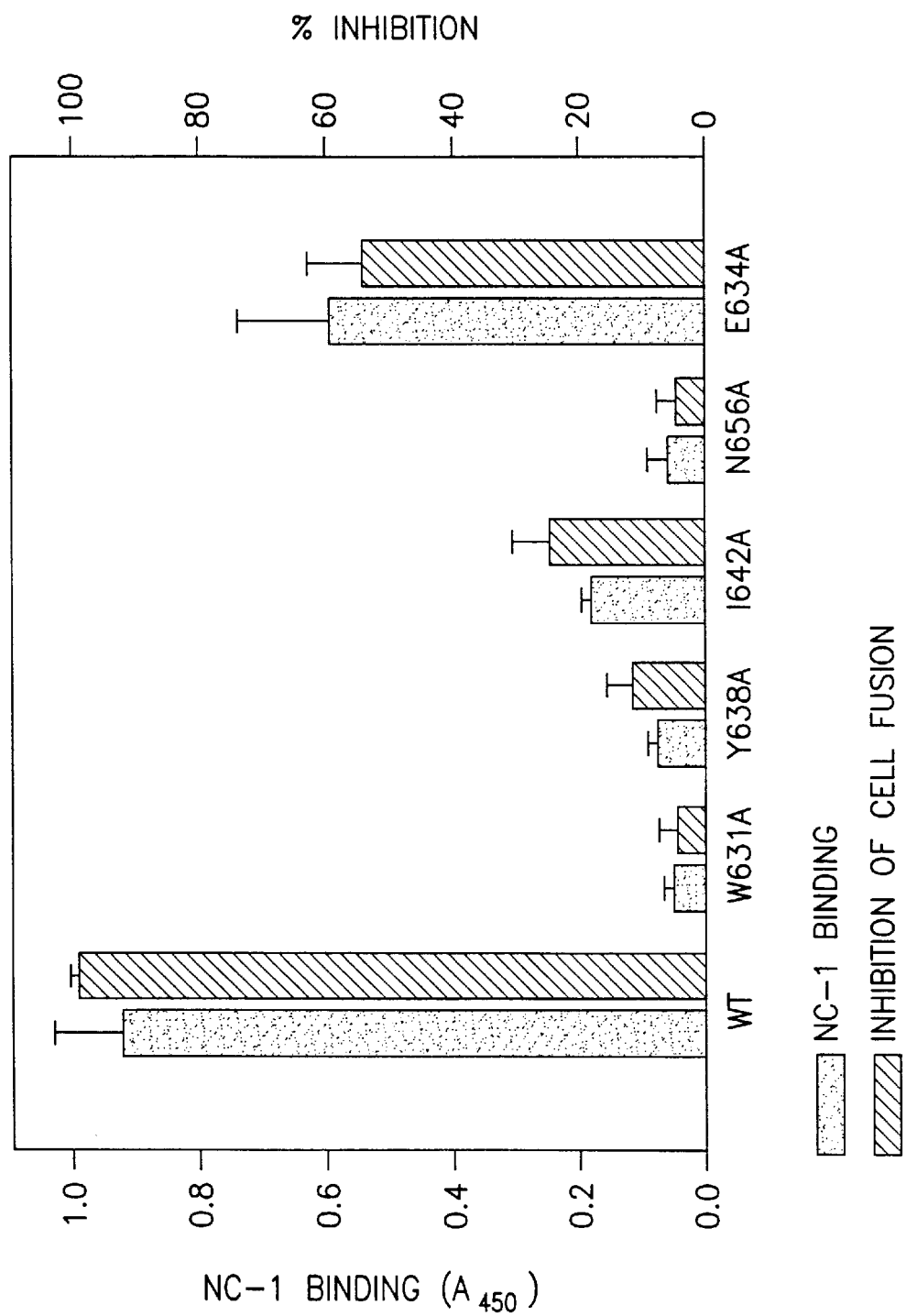
FIG. 11 is a graph showing the activity of SJ-2176 and its mutants to inhibit HIV-mediated cell fusion and to form NC-1 detectable complexes with N-36.

Single-point Mutations in C-peptides that Abolish Their Ability to Form Complexes with N-36 also Eliminate Their Inhibitory Activity on HIV-1-Mediated Cell Fusion As discussed hereinbefore, the conserved residues at the "a" and "d" positions in the wheel of a C helix interact with those at the "e" and "g" positions of N helices to form the hair-pin coiled-coil structure (FIG. 1B) which is critical for membrane fusion. Similarly, C peptides may also interact with the N helix in gp41 via those key residues to inhibit membrane fusion. To determine whether or not single-point mutations of these residues affect antibody recognition and inhibitory activity on HIV-1 infection, several residues at the "a" and "d" positions in a C-peptide SJ-2176 were replaced by alanines (W631A, Y638A, I647A, and N656A). One peptide containing a mutation at the "g" position (E634A) and the wild-type peptide (WT) were used as controls. As shown in FIG. 11, all the peptides with mutations at the "a" and "d" positions almost completely lost their inhibitory activity on cell fusion and failed to form complexes detectable by MAb NC-1, while the activity of the peptide with a mutation at the "g" position only partially decreased, suggesting that single-point mutations at the key interaction sites in the C-peptides abolish inhibitory effects on membrane fusion and reactivity with NC-1. With respect of FIG. 11, NC-1 binding to the peptide complexes was determined in the sandwich ELISA with the same conditions described in FIG. 10. The inhibitory activity of the peptides (1 $\mu$M) on HIV-1 infection was detected in a cell fusion assay.

Figure 12:
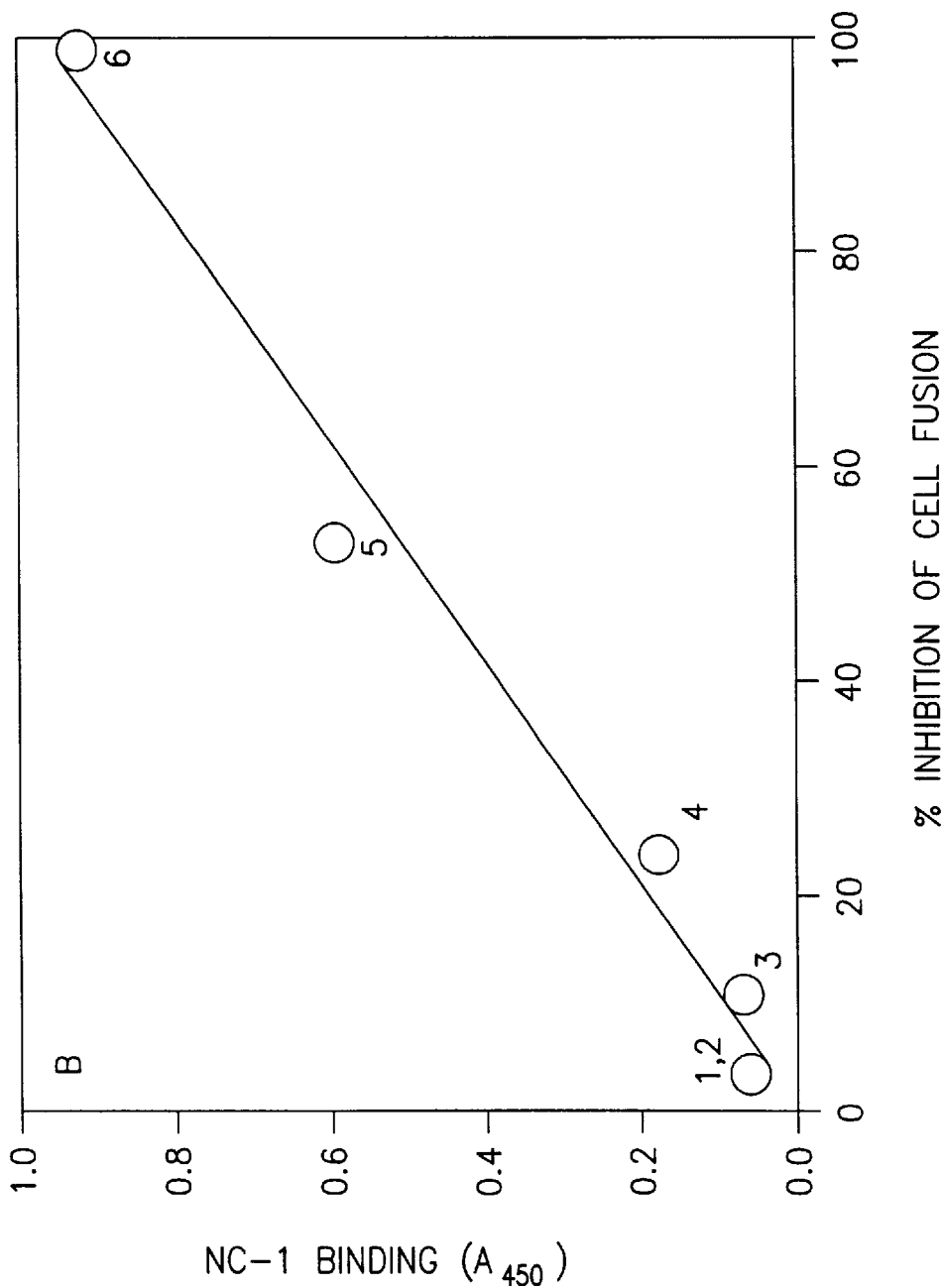
FIG. 12 is a graph showing the correlation between the inhibitory activity of SJ-2176 and its mutants on HIV-1-mediated cell fusion and their ability to form NC-1 detectable complexes with N-36 (points 1 to 6 represent peptides W631A, W656A, Y638A, I642A, E634A and WT, respectively).

The fusion inhibitory activity of C-peptides is correlated with their ability to interact with the N-peptide to form a complex (r=0.988) (FIG. 12).

Figure 13:
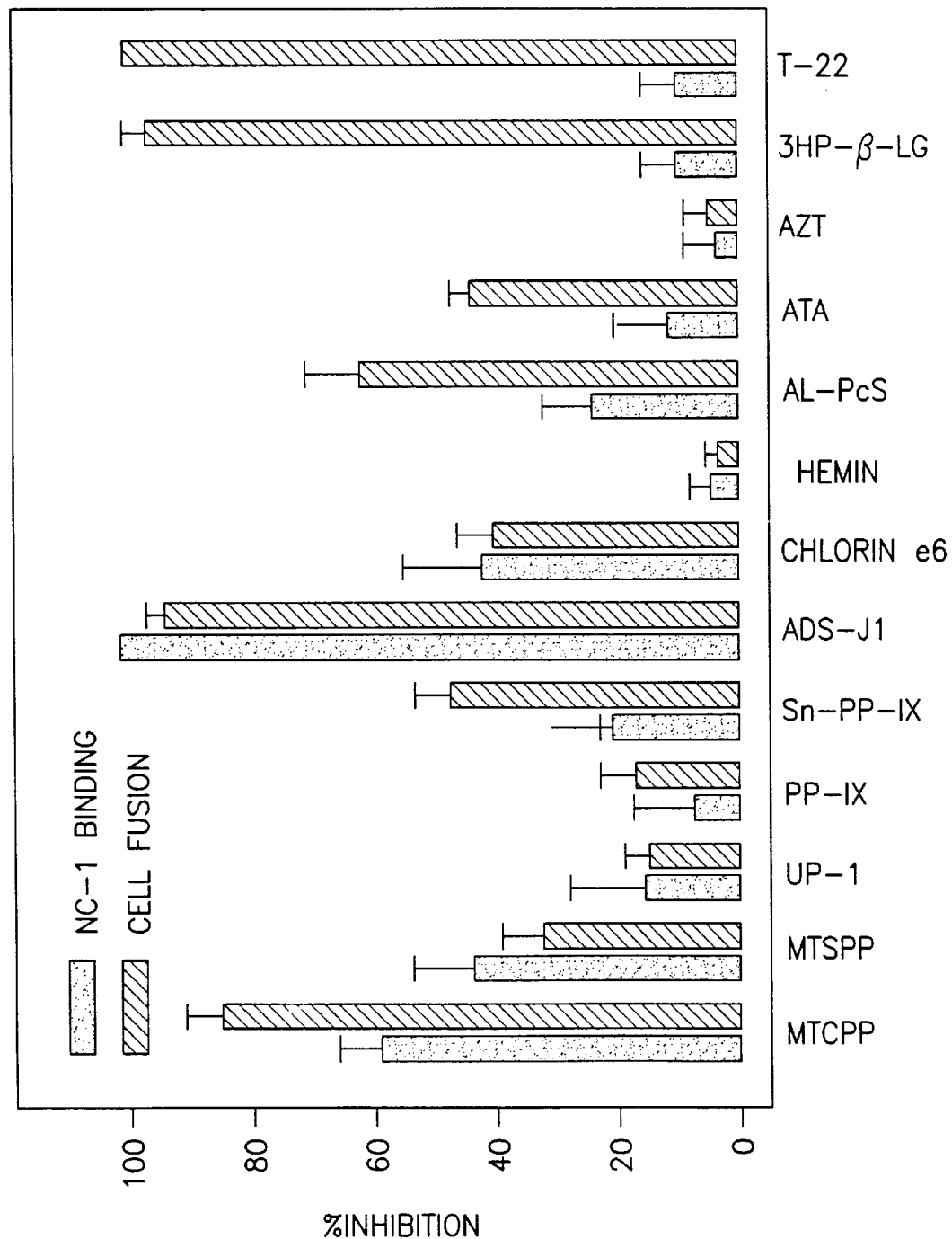
FIG. 13 is a graph showing the inhibitory activity of compounds on the formation of the N-36/C-34 complex and on HIV-1-mediated cell fusion. The compounds (10 μg/ml) were tested by the sandwich ELISA and a cell fusion assay described hereinbelow.
Figure 14D:
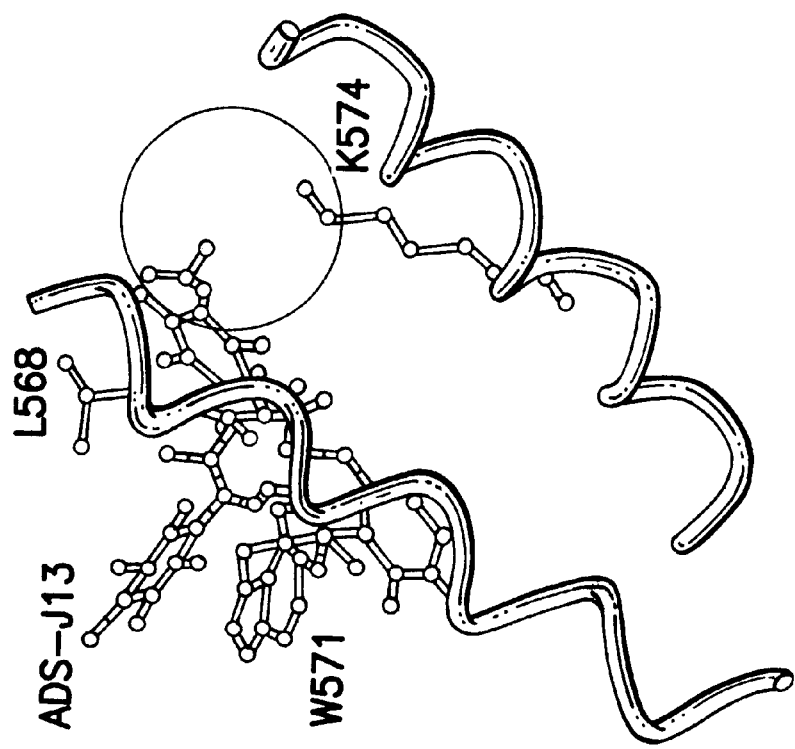
Figure 14C:
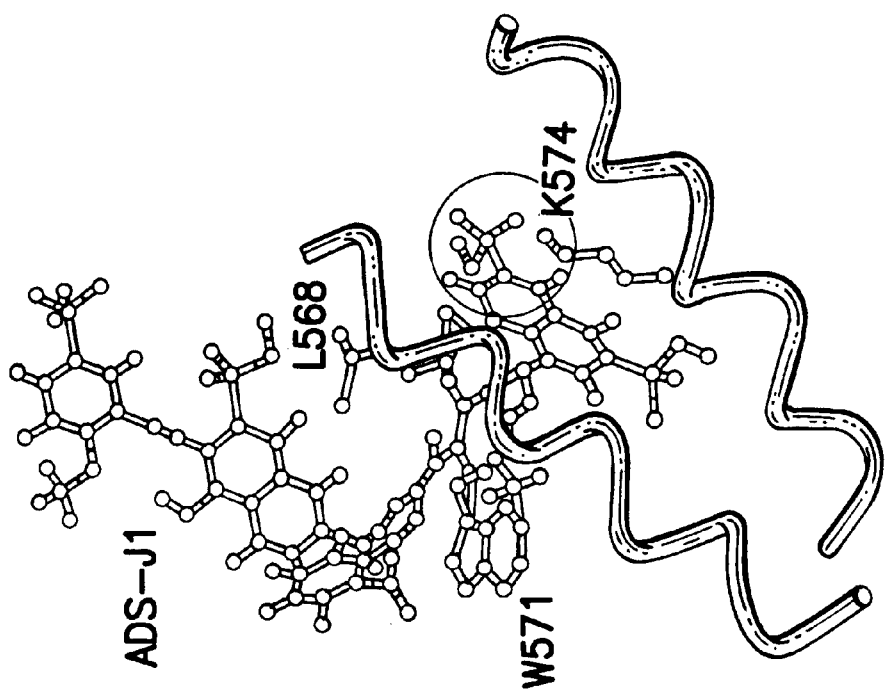
Figure 15:
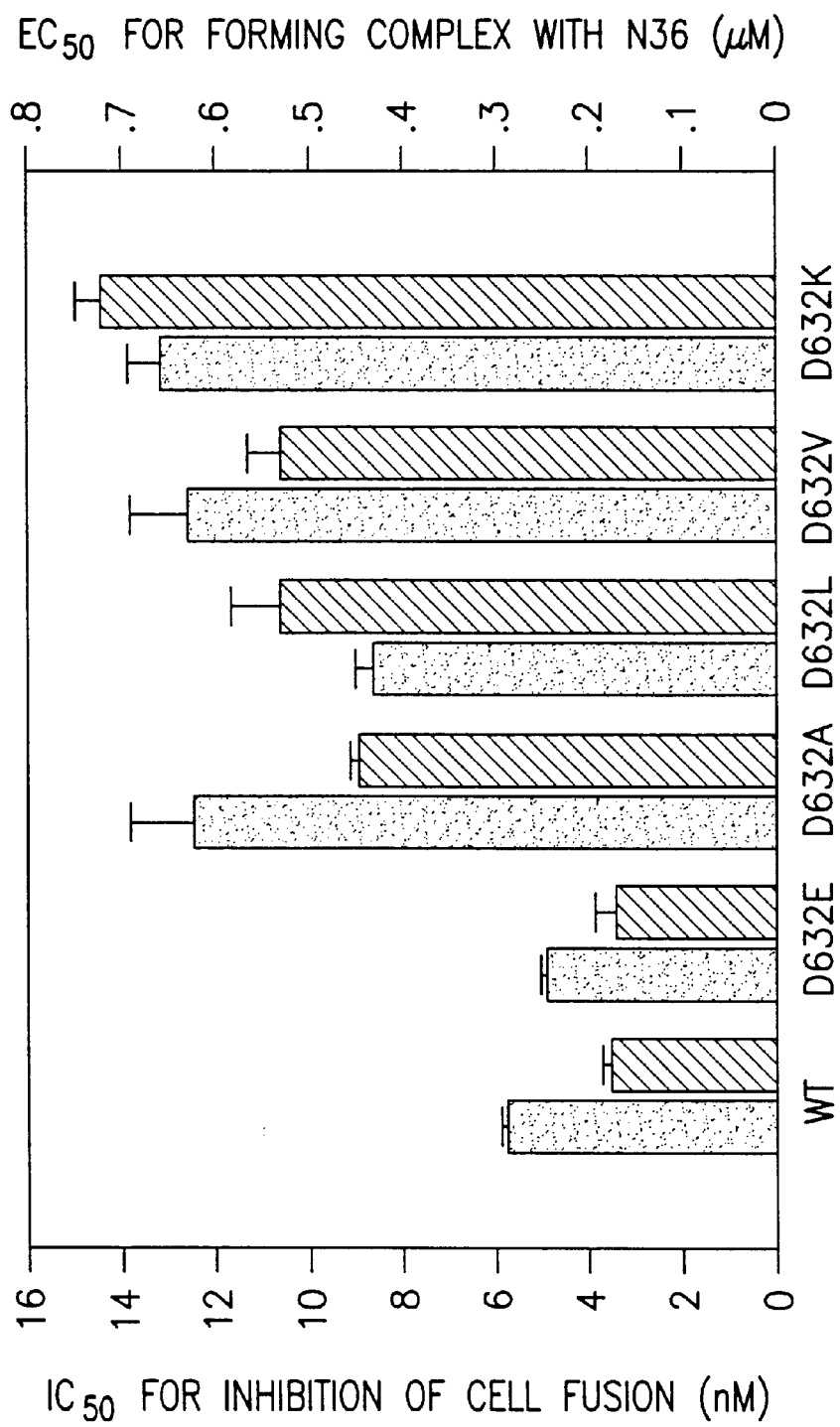
FIG. 15 is a graph showing the activity of peptide C34 and its analogues to inhibit HIV-1-mediated cell fusion (shaded bars) and to form NC-1 detectable complexes with N36 (bars with diagonal lines). A fluorescent dye transfer assay was used for detection of HIV-1-mediated cell fusion (Jiang, S., K. Lin, N. Strick, and A. R. Neurath, 1993, "HIV-1 inhibition by a peptide", Nature, 365, 113). A sandwich ELISA was applied for determination of the activity of C-peptides to form complexes with N36 (Jiang, S., K. Lin, L. Zhang, and A. K. Debnath, 1999, "A Screening Assay for Antiviral Compounds Targeted to the HIV-1 gp41 Core Structure Using a Conformation-specific Monoclonal Antibody", J. Virol. Methods, 80, 85–96).

Screening of Compounds for Their Potential Inhibitory Activity on Complex Formation by N-36 and C-34 and on HIV-1-Mediated Cell Fusion Using MAb NC-1 in the sandwich ELISA described hereinabove, a series of compounds at 10 $\mu$g/ml were tested for their possible inhibitory activity on complex formation by N-36 and C-34 and on HIV-1-mediated cell fusion. As shown in FIG. 13, several compounds significantly inhibited cell fusion, but did not block NC-1 detectable complex formation by the N-36 and C-34. Several porphyrin derivatives, such as MTCPP, MTSPP and chlorin e6, partially inhibited, while 7-[6-phenylamino-4-[4-[(3,5-disulfo-8-hydroxynaphthyl)azo]-2-methoxy-5-methylphenylamino]-1,3,5-triazine-2-yl]-4-hydroxy-3-[(2-methoxy-5-sulfophenyl)azo]-2-naphthalene sulfonic acid completely inhibited both NC-1 binding and cell fusion. These results indicate that 7-[6-phenylamino-4-[4-[(3,5-disulfo-8-hydroxynaphthyl)azo]-2-methoxy-5-methylphenylamino]-1,3,5-triazine-2-yl]-4-hydroxy-3-[(2-methoxy-5-sulfophenyl)azo]-2-naphthalene sulfonic acid and several other porphyrin derivatives block HIV-1-mediated membrane fusion by interfering with formation of the six-stranded complex formed by the N and C helices within gp41.

Example 3

Structure-Based Identification of Small Molecule Antiviral Compounds Targeted to the gp41 Core Structure of HIV-1

Cells, Viruses and Antibodies

MT-2 cells, HIV-1$_{IIIB}$ infected H9 cells (H9/HIV-1$_{IIIB}$) and the HIV-1$_{IIIB}$ isolate were obtained from the NIH AIDS Research and Reference Reagent Program. Rabbit polyclonal antibody (PAb) and the mouse monoclonal antibody (MAb) NC-1 directed against the recombinant N36(L6)C34 polypeptide were utilized. Rabbit and mouse IgG were purified using protein-A kits (Pierce, Rockford, Ill.).

Peptides and Compounds

Peptides were synthesized by a standard solid-phase FMOC method. The N-termini of the peptides were acetylated and their C-termini were amidated. The peptides were purified to homogeneity by high-performance liquid chromatography (HPLC). The identity of the purified peptides was confirmed by laser desorption mass spectrometry (PerSeptive Biosystems). The small organic compounds (ADS-J1 to ADS-J16) tested were purchased from ComGenex, Inc. (Budapest, Hungary). The chemical structure of these compounds are shown in the following TABLE 1.

TABLE 1

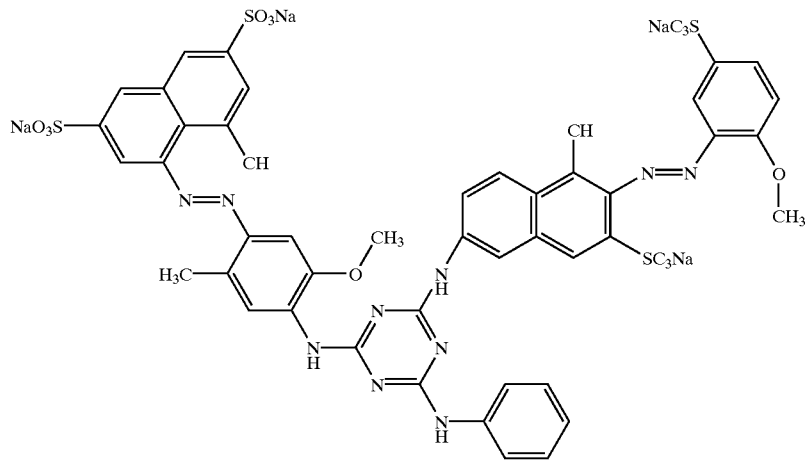
ADS-J1

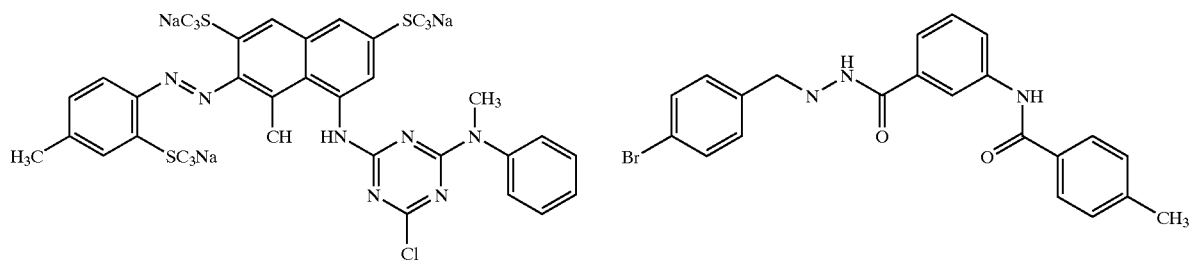
ADS-J3

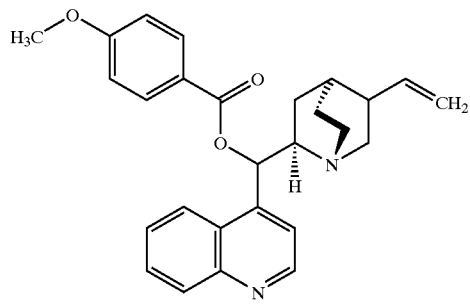
ADS-J4

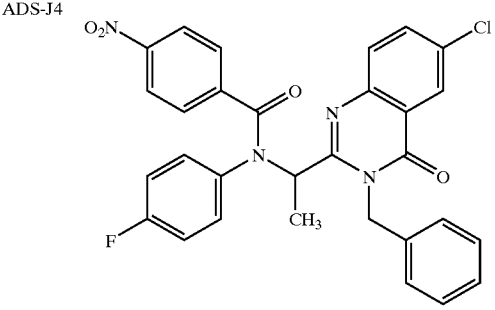
ADS-J5

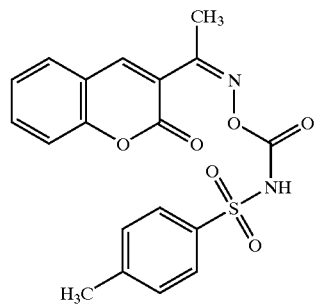
ADS-J6

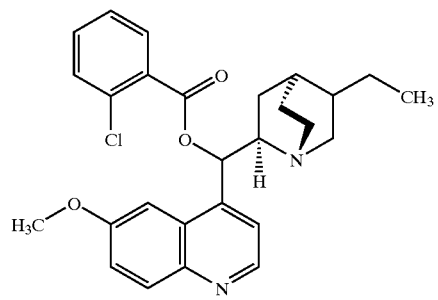
ADS-J7

ADS-J8
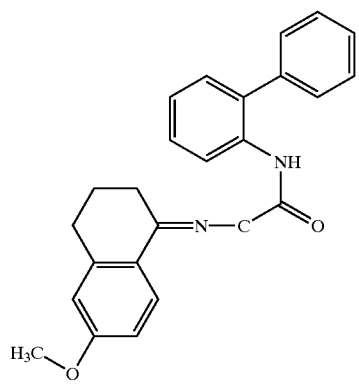
ADS-J9
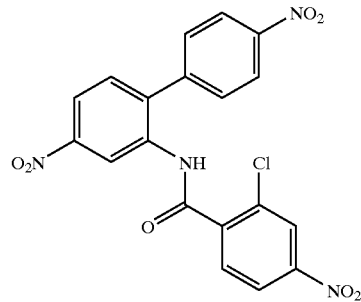
ADS-J10
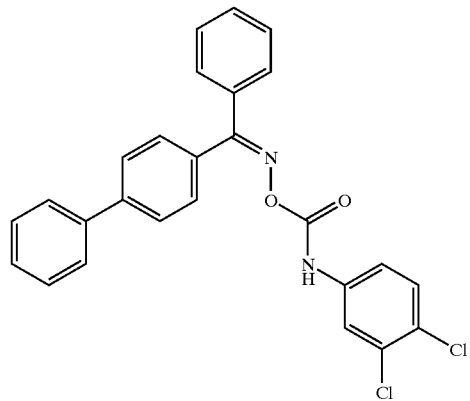
ADS-J11
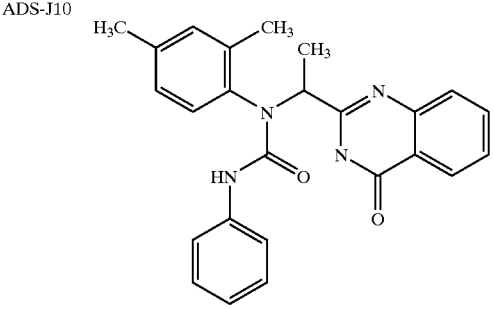
ADS-J12
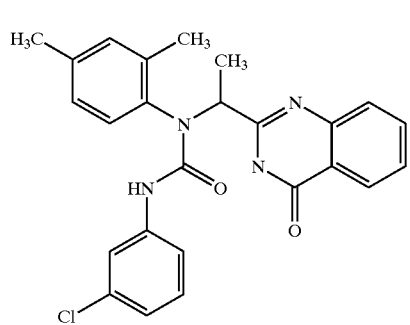
ADS-J13
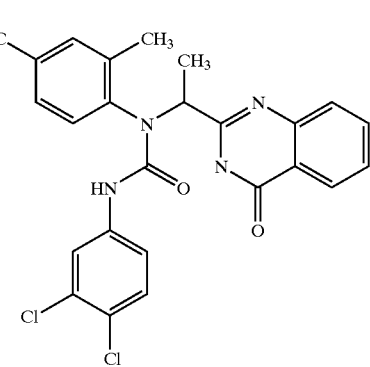
ADS-J14
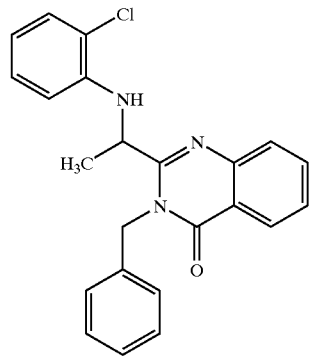
ADS-J15
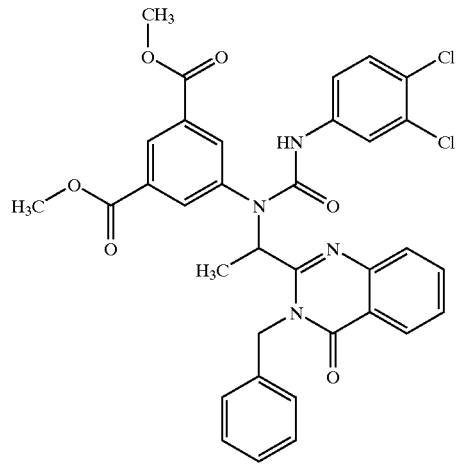

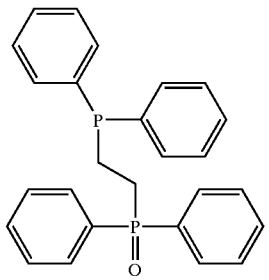

ADS-J16

Hardware and Software

A Silicon Graphics Indigo Extreme computer was used for all molecular modeling studies. The DOCK 3.5 Suit of programs (DesJarlais, R. L., R. P. Sheridan, G. L. Seibel, L. S. Dixon, I. D. Kuntz,. and R. Venkataraghavan, 1988, "Using shape complementarity as an initial screen in designing ligands for a receptor binding site of known three-dimensional structure", J. Med. Chem., 31, 722–729; Shoichet, B. K., D. L. Bodian, and I. D. Kuntz, 1992, Molecular docking using shape descriptors, J. Comp. Chem., 13, 380–397) was used for automated docking simulations. SYBYL 6.5 from Tripos Associates, Inc. (SYBYL 6.5, Tripos Associates Inc., 1699 South Hanley Road, St. Louis, Mo. 63144, USA, (6.5), 1998) was used for all other modeling purposes including molecular visualizations. CrystalEyes2 (CrystalEyes, Stereographic Corp., 2171 East Francisco Blvd., San Rafel, Calif. 94901, USA) stereographic eye glasses were used along with SYBYL 6.5 software for stereo visualization. CONCORD 4.0. (Pearlman, R. S., CONCORD 4.0 User's Manual, (4.0.2), 1998, St. Louis, Mo.), distributed by Tripos Associates Inc. was used to generate three dimensional structures of the compounds used for molecular docking studies.

Automated Docking of Small Molecules to the Hydrophobic Cavity of the gp41 Core Structure The DOCK suit of programs has been successfully used to identify lead compounds against several targets and the methods have been described in great detail (Ring, C. S., E. Sun, J. H. McKerrow, G. K. Lee, P. J. Rosenthal, I. D. Kuntz, and F. E. Cohen, 1993, "Structure-based inhibitor design by using protein models for the development of antiparasitic agents", Proc. Natl. Acad. Sci. USA, 90, 3583–3587; Rutenber, E., E. B. Fauman, R. J. Keenan, S. Fong, P. S. Furth, P. R. Ortiz de Montellano, E. Meng, I. D. Kuntz, D. L. DeCamp, R. Salto, J. R. Rose, C. Craick, and R. M. Stroud, 1993, "Structure of a non-peptide inhibitor complexed with HIV-1 protease, Developing a cycle of structure-based drug design", J. Biol. Chem., 268, 15343–15346; Shoichet, B. K., R. M. Stroud, D. V. Santi, I. D. Kuntz, and K. M. Perry, 1993, "Structure-based discovery of inhibitors of thymidylate synthase", Science, 259, 1445–1450). The important steps for docking using these programs are as follows:

(1) Identification of the target site in a well defined receptor structure (preferably, X-ray crystal structures but NMR and homology modeled structures are also used).

(2) Creation of the molecular surface of the target site.

(3) Identification of the important residues for possible interaction with the ligand molecule.

(4) Generation of spheres to fill the active site that serve as the guide to locate ligands whose inter-atomic distance matches the intersphere-center distance.

(5) Generation of a grid box encompassing the spheres to save the steric and electrostatic information at each grid point so that the ligand orientation can be scored during docking.

(6) Searching of thousands of orientations of ligands to match the center of the spheres.

(7) Evaluation of the ligand orientation by shape or force-field scoring function. The shape scoring function resembles van der Waals attractive energy, whereas the force-field scoring function approximates at best an interaction enthalpy and is approximately the sum of van der Waals attractive, dispersive and Coulombic electrostatic energies.

(8) Location of local minima by simplex minimization.

The DOCK suit of programs was used to screen one commercially available database from ComGenex, Inc., Budapest, Hungary, consisting of 20,000 small molecule compounds. The 3D coordinates of the small molecules were generated by the CONCORD program.

One of the C-helices from the coiled-coil trimer of heterodimers was removed to generate the target site on the N-peptide for the docking of small molecule compounds. According to information from X-ray crystallography, two indole rings from the C-peptide (Trp-628 and Trp-631) dock into a deep hydrophobic cavity. The negative image of this cavity (target site) was created by selecting all residues (8.0 Å radius) surrounding Trp-628. The molecules were then docked into the cavity and the quality of the ligand binding was evaluated by a force-field scoring function. Two hundred top scoring compounds were selected for further analysis by visual inspection using the SYBYL program, and stereoscopic eye wears (CrystalEyes). Irrespective of the score, 20 compounds with the best fit and maximum possible interactions (hydrophobic, electrostatic, H-bond, etc.) with the target site were selected for biological assays (16 compounds were available from the supplier and their chemical structures are shown in TABLE 1).

ELISA

A sandwich ELISA was established to screen for compounds that interfere with the formation of the N-36/C-34 complex. N-36 (2 $\mu$M) was preincubated with compounds at graded concentrations at 37° C. for 30 minutes, followed by the addition of C-34 (2 $\mu$M). After incubation at 37° C. for 30 minutes, the mixture was added to wells of a 96-well polystyrene plate (Immulon I, Dynatech Laboratories, Inc., Chantilly, Va.) which were precoated with IgG (10 $\mu$g/ml) purified from rabbit antisera directed against N36(L6)C34. Then, the MAb NC-1, biotin-labeled goat-anti-mouse IgG (Boehringer Mannheim), streptavidin-labeled horseradish peroxidase (Zymed, San Francisco, Calif.), and the substrate, 3,3',5,5'-tetramethylbenzidine (Sigma Chemical Co., St. Louis, Mo.) were added sequentially. Absorbance at 450 nm ($A_{450}$) was read using an ELISA reader (Dynatech Laboratories, Inc., Chantilly, Va.). The percentage of inhibition by the compounds of the binding of NC-1 to the peptide complexes was calculated as described in Jiang S., K. Lin, and A. R. Neurath, 1991, "Enhancement of human immunodeficiency virus type-1 (HIV-1) infection by antisera to peptides from the envelope glycoproteins gp120/gp41", *J. Exp. Med.*, 174, 1557–1563. The concentration for 50% inhibition ($IC_{50}$) was calculated using a computer program, designated Calcusyn (Chou, T.-C., 1991, "The median-effect principle and the combination index for quantitation of synergism and antagonism. In Synergism and Antagonism in Chemotherapy", T.-C. Chou and D. C. Rideout, editors, Academic Press, San Diego, 61–102).

HIV-1-Mediated Cell Fusion

A dye transfer assay was used for detection of HIV-1 mediated cell fusion as described in Jiang, S., K. Lin, N. Strick, and A. R. Neurath, 1993, Inhibition of HIV-1 infection by a fusion domain binding peptide from HIV-1 envelope glycoprotein gp41, *Biochem. Biophys. Res. Commun.*, 195, 533–538.

H9/HIV-1$_{IIIB}$ cells were labeled with a fluorescent reagent, 2',7'-bis-(2-carboxyethyl)-5-and-6-carboxyfluorescein acetoxyethyl ester (BCECF-AM) (Molecular Probes, Inc., Eugene, Oreg.) and then incubated with MT-2 cells (ratio=1:10) in 96-well plates at 37° C. for 2 hours in the presence or absence of the compounds tested. The fused and unfused BCECF-labeled HIV-1 infected cells were counted under an inverted fluorescence microscope (Zeiss, Germany) with an eyepiece micrometer disc. The percentage of inhibition of cell fusion and the $IC_{50}$ values were calculated as described in Jiang et al., (1993), *Biochem. Biophys. Res. Commun.*, 195, 533–538.

Detection of HIV-1-Mediated Cytopathic Effect (CPE) and of in vitro Cytotoxicity The inhibitory activity of the compounds was determined by a calorimetric method based on protection of cells against HIV-1-mediated CPE, as described in Jiang et al., (1991), *J. Exp. Med.*, 174, 1557–1563. $1 \times 10^4$ MT-2 cells in 96-well plates were infected with diluted HIV-1$_{IIIB}$ in 200 µl RPMI 1640 medium containing 10% FBS in the presence of compounds at graded concentrations. After 1 hour, 24 hours and 4 days, half of the culture media were changed. On the sixth day post infection, an indicator, XTT tetrazolium dye (1 mg/ml; 50 µl/well; PolySciences, Inc., Warrington, Pa.), was added to the cells. After 4 hours, the soluble intracellular formazan was determined calorimetrically at 450 nm. The percent of inhibition of CPE and the $IC_{50}$ values were calculated as described above.

The in vitro cytotoxicity for MT-2 cells of the compounds was determined in 96-well plates using the XTT dye to measure cell viability in the absence of virus. Ten µl of 5% TRITON X-100 were added to the wells corresponding to positive controls ("P") and 10 µl medium was added to wells corresponding to negative controls ("N"). The percent cytotoxicity was calculated using the following formula: % cytotoxicity=[(E−N)/(P−N)]×100%, wherein "E" represents experimental data in the presence of compounds. The concentration corresponding to 50% cytotoxicity ($CC_{50}$) for MT-2 cells was calculated using the Calcusyn computer program. The selectivity index (S.I.=$CC_{50}/IC_{50}$) for each compound was calculated.

Results

Recent determination of the X-ray crystal structures of the gp41 core and identification of a deep hydrophobic pocket within the core opened up a new avenue to target this site for structure-based drug design. As gp41 plays an important role in fusion of the HIV-1 envelope with the target cell membrane, inhibition of this early event may lead to inhibition of infection. Drugs targeted to this site are considered to be useful against mutant viruses resistant to RT and/or protease inhibitors. Though high throughput screening (HTS) and combinatorial libraries have paved the way for rapidly screening millions of compounds in a short period of time (Lebl, M., 1999, "Parallel personal comments on 'classical' papers in combinatorial chemistry", *J. Comb. Chem.*, 1, 3–24; Kubinyi, H., 1995, Strategies and recent technologies in drug discovery, Pharmazie, 50, 647–662; Bevan, P., H. Ryder, and I. Shaw, 1995, "Identifying small-molecule lead compounds: the screening approach to drug discovery", *Trends. Biotechnol.*, 13, 115121), it requires substantial resources and is not cost-effective if libraries are not designed rationally. Structure-based drug design by docking has shown promise when using large library for screening (Selzer, P. M., X. Chen, V. J. Chan, M. Cheng, G. L. Kenyon, I. D. Kuntz, J. A. Sakanari, F. E. Cohen, and J. H. McKerrow, 1997, "Leishmania major: molecular modeling of cysteine proteases and prediction of new nonpeptide inhibitors", *Exp. Parasitol*, 87, 212–221; Chen, Q., R. H. Shafer, and I. D. Kuntz, 1997, "Structure-based discovery of ligands targeted to the RNA double helix", *Biochemistry*, 36, 11402–11407; Good, A. C., T. J. Ewing, D. A. Gschwend, and I. D. Kuntz, 1995, "New molecular shape descriptors: application in database screening", *J. Comput. Aided Mol. Des.*, 9, 1–12; Kuntz, I. D., 1992, Structure-based strategies for drug design and discovery, *Science*, 257, 1078–1082). This theoretical screening method, if judiciously used, may screen out compounds that interact effectively with the target sites.

Using computer-aided molecular docking by the DOCK suit of programs, a database of 20,000 small organic molecules were screened for compounds which dock into the deep hydrophobic cavity on the trimer created by three N-helices. The force-field scoring method was used to rank best possible compounds for docking potentials into the cavity instead of just shape based scoring method because other charged groups surrounding this cavity may also play important role in interacting with ionic groups present in the inhibitor molecules. Two hundred top scoring compounds were selected from a dock run for in-depth inspection of the interactions at the hydrophobic cavity and neighboring regions by molecular visualization techniques. The dock scores cannot be a quantitative predictor of activity because many approximations are involved in its search technique and scoring methods. Therefore, close visual inspection with stereo glasses of the top scoring molecules individually for appropriate interactions is necessary (Gschwend, D. A., W. Sirawaraporn, D. V. Sand, and I. D. Kuntz, 1997, "Specificity in structure-based drug design: Identification of a novel, selective inhibitor of Pneumocystis carinii dihydrofolate reductase", *Proteins*, 29, 59–67).

Sixteen of the 200 best scoring compounds were tested by ELISA for inhibitory activity on the formation of the N-36/C-34 complex using MAb NC-1 and on HIV-1 infection, including HIV-1 mediated cell fusion and CPE and for in vitro cytotoxicity. Two of the compounds, namely, 7-[6-phenylamino-4-[4-[(3,5-disulfo-8-hydroxynaphthyl)azo]-2-methoxy-5-methylphenylamino]-1,3,5-triazine-2-yl]-4-hydroxy-3-[(2-methoxy-5-sulfophenyl)azo]-2-naphthalene sulfonic acid (ADS-J1) and 5-[(4-chloro-6-phenylamino-1,3,5-triazine-2-yl)an-amino]-4-hydroxy-3-[(4-methyl-6-sulfophenyl)azo]-2,7-naphthalene disulfonic acid (ADS-J2), have promising inhibitory activity against the formation of MAb NC-1 detectable N-36/C-34 complex and against HIV-1 mediated cell fusion and CPE.

Example 4

Salt Bridges Between an N-terminal Coiled Coil of gp41 and Antiviral Agents Targeted to the gp41 Core are Important for Anti-HIV-1 Activity Compound ADS-J13 [N'-(3,4-dichlorophenyl)-N-[1-(4-oxo-3,4-dihydroquinazolin-2-yl)ethyl]-N-2,4-dimethyl phenylurea] had a higher docking score than compounds ADS-J1 and ADS-J2, but it had no HIV-1 inhibitory activity. It was of interest to know why ADS-J13, unlike ADS-J1, does not inhibit HIV-1 mediated cell fusion. Computer-aided modeling analyses indicated that all the compounds studied had the potential to dock into the deep hydrophobic pocket on the surface of the central N-helix core. Close visual inspection of the possible interaction pattern of these compounds by 3D stereoscopic eye glasses revealed that ADS-J1 was positioned in such a way that its hydrophobic groups (phenyl and naphthalene) were able to interact with the hydrophobic residues (Leu 568, Val 570, Trp 571) in the pocket. In addition, one of its negatively charged groups (sulfonic acid groups) is in close proximity to a positively charged group of Lys 574 in the N-helix located outside the pocket (FIG. 14C), suggesting that these two oppositely charged groups can interact with each other to form a salt bridge. ADS-J2 also has a similar positively charged group to interact with Lys 574 in the N-helix. Compounds ADS-J3 to ADS-J16 have hydrophobic groups, which may interact with the hydrophobic residues in the pocket, but they do not have any negatively charged group to interact with Lys 574 (only ADS-J13 is shown in FIG. 14D as an illustrative example). Though this ionic interaction is not expected to fully explain the inactivity of these compounds, it suggests that along with hydrophobic groups, negatively charged group(s) may be important to interact with a positively charged residue, especially Lys 574, in the surrounding areas to form a salt bridge. This interaction may play a key role to maintain the compounds in appropriate positions so that they can effectively block the interaction between the N- and C-terminal HR regions to form the gp41 core.

The C-terminal HR region of gp41 may also need a negatively charged residue at the right position to interact with Lys 574 in the N-helix to form a salt bridge. Analysis of the crystal structure of the gp41 core reveals that the C-terminal HR region indeed contains an Asp at position 632 which is in close proximity to Lys 574 in the N-helix (FIG. 14A) (Chan D. C., D. Fass, J. M. Berger, and P. S. Kim, 1997"Core Structure of gp41 form the HIV Envelope Glycoprotein", *Cell,* 89, 263–273). Analyzing the currently available HIV-1 gp41 sequences, it was found that both the Lys 574 and Asp 632 in gp41 are highly conserved. Out of 214 sequences analyzed, 100% of the sequences contain positively charged residues (Lys or Arg) at positions corresponding to Lys 574 in the HIV-$1_{HXB2}$ and 98% of the sequences have negatively charged residues (Asp or Glu) at positions corresponding to Asp 632 in the HIV-$1_{HXB2}$ (Korber, B., C. Kuiken, B. Foley, B. Hahn, F. McCutchan, J. Mellors, J. Sodroski, 1998, "Human Retroviruses and AIDS 1998", p. I-1–III-265, Los Alamos Laboratory, Los Alamos, N.M.). These data indicate that these highly conserved, oppositely charged residues located in the N- and C-terminal HR regions of gp41 may play an important role in HIV-1 mediated membrane fusion and in C-peptide-mediated inhibition of HIV-1 infection (Jiang, S., K. Lin, N. Strick, and A. R. Neurath, 1993, "HIV-1 Inhibition by a Peptide", *Nature,* 365, 113; Kilby, J. M., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag, 1998, "Potent Suppression of HIV-1 Replication in Humans by T-20, A Peptide Inhibitor of gp41-Mediated Virus Entry", *Nature Med.,* 4, 1302–1307; Wild, C. T., D. C. Shugars, T. K. Greenwell, C. B., McDanal, T. J. Matthews, 1994, "Peptides Corresponding to a Predictive Alpha-Helical Domain of Human Immunodeficiency Virus Type 1 gp41 are Potent Inhibitors of Virus Infection", *Proc. Natl. Acad. Sci. USA,* 9, 9770–9774).

In order to further verify the above, a series of C34 peptide analogues were synthesized by replacement of Asp 632 with Glu (D632E), Lys (D632K), Leu (D632L), Val (D632V), and Ala (D632A), respectively. Their activity to inhibit HIV-1-mediated cell fusion and to form NC-1 detectable complexes with N36 was compared. As shown in FIG. 15, a conserved mutation of Asp 632 with a negatively charged residue Glu (D632E) did not change the inhibitory activity of cell fusion and the ability to form a complex with N36. However, replacement of Asp 632 with a positively charged residue Lys (D632K) and with hydrophobic residues Leu and Val (D632L and D632V), as well as with Ala (D632A) resulted in significant decrease of activity of the corresponding peptides to inhibit HIV-1 infection and to form complexes with N36. These results confirm that the salt bridge formed between the negatively charged residue at position 632 in a C-peptide, or the acidic groups in antiviral compounds, and the positively charged residue at the position 574 in the N-terminal HR region is important for the C-peptide or the antiviral compound-mediated inhibitory activity against HIV-1-mediated membrane fusion.

TABLE 2

Inhibitory activities of compounds selected from the ComGenex database by docking to the cavity within the gp41 core domain.

| Compounds | Molecular Weight | $CC_{50}^1 \pm SD$ (μg/ml) | $IC_{50}^2 \pm SD$ (μg/ml) NC-1 binding | Cell fusion | CPE | Selective Index[3] |
|---|---|---|---|---|---|---|
| ADS-J1 | 1177 | 292.16 ± 2.27 | 0.73 ± 0.08 | 4.95 ± 1.31 | 8.29 ± 1.13 | 35.24 |
| ADS-J2 | 802 | 289.94 ± 12.39 | 3.18 ± 0.36 | 21.85 ± 1.38 | 30.76 ± 6.74 | 9.43 |
| ADS-J3 | 436 | 24.91 ± 2.62 | >100 | >100 | >100 | ≦1.00 |
| ADS-J4 | 429 | 74.12 ± 0.76 | >100 | >100 | >100 | ≦1.00 |
| ADS-J5 | 557 | 30.17 ± 4.84 | >100 | >100 | >100 | ≦1.00 |
| ADS-J6 | 400 | 285.98 ± 19.31 | >100 | >100 | >100 | ≦1.00 |
| ADS-J7 | 465 | 41.33 ± 2.38 | >100 | 59.78 ± 8.69 | >100 | ≦1.00 |
| ADS-J8 | 386 | 46.83 ± 4.93 | >100 | >100 | >100 | ≦1.00 |
| ADS-J9 | 443 | 47.22 ± 5.48 | >100 | >100 | >100 | ≦1.00 |

TABLE 2-continued Inhibitory activities of compounds selected from the ComGenex database by docking to the cavity within the gp41 core domain.

| Compounds | Molecular Weight | $CC_{50}{}^1 \pm SD$ ($\mu$g/ml) | $IC_{50}{}^2 \pm SD$ ($\mu$g/ml) | | | Selective Index[3] |
|---|---|---|---|---|---|---|
| | | | NC-1 binding | Cell fusion | CPE | |
| ADS-J10 | 461 | 74.67 ± 6.04 | >100 | >100 | >100 | ≤1.00 |
| ADS-J11 | 412 | 40.77 ± 1.67 | >100 | >100 | >100 | ≤1.00 |
| ADS-J12 | 447 | 54.02 ± 8.14 | >100 | >100 | >100 | ≤1.00 |
| ADS-J13 | 481 | 39.22 ± 7.60 | >100 | >100 | >100 | ≤1.00 |
| ADS-J14 | 390 | 86.82 ± 5.79 | >100 | >100 | >100 | ≤1.00 |
| ADS-J15 | 660 | 20.95 ± 0.67 | >100 | >100 | >100 | ≤1.00 |
| ADS-J16 | 414 | 28.88 ± 5.97 | >100 | 52.27 ± 2.85 | >100 | ≤1.00 |

[1]$CC_{50}$ = 50% cytotoxic concentration;
[2]$IC_{50}$ = 50% inhibitory concentration;
[3]Selective index (S.I.) = $CC_{50}/IC_{50}$ for CPE.

It will be appreciated that the instant specification is set forth by way of illustration and not limitation, and that various modifications and changes may be made without departing from the spirit and scope of the present invention.

What is claimed is:

1. A method for the screening of antiviral compounds comprising:
   (a) capturing polyclonal antibodies from an animal other than a mouse, directed against the HIV-1 gp41 trimeric structure containing three N-peptides of HIV-1 gp41 and three C-peptides of HIV-1 gp41, onto a solid-phase to form a polyclonal antibody coated solid-phase,
   (b) forming a mixture of a compound to be tested with N-peptides of HIV-1 gp41, and then adding C-peptides of HIV-1 gp41,
   (c) adding the mixture from step (b) to the polyclonal antibody coated solid-phase from step (a), then removing unbound peptides and unbound compound, and then adding a monoclonal antibody which specifically reacts with the HIV-1 gp41 trimeric structure containing three N-peptides of HIV-1 gp41 and three C-peptides of HIV-1 gp41, but does not react with individual N-peptides of HIV-1 gp41 and does not react with individual C-peptides of HIV-1 gp41, and
   (d) measuring the binding of said monoclonal antibody.

2. The method of claim 1, wherein the measuring of the binding of said monoclonal antibody in step (e) is carried out by sequentially adding biotin labeled anti-mouse IgG, streptavidin or avidin labeled enzyme, and a substrate for generating detectable color.

3. The method of claim 1, wherein the polyclonal antibody is rabbit IgG and the solid-phase is a polystyrene plate having a plurality of wells.

4. The method of claim 1, wherein the monoclonal antibody is NC-1, the N-peptide of HIV-1 gp41 is N-36 and the C-peptide of HIV-1 gp41 is C-34.

* * * * *